(12) United States Patent
Kanner et al.

(10) Patent No.: US 7,758,610 B2
(45) Date of Patent: *Jul. 20, 2010

(54) ADVANCED WOUND SITE MANAGEMENT SYSTEMS AND METHODS

(75) Inventors: Glenn Kanner, Plymouth, MA (US); Kenneth Arden Eliasen, East Bridgewater, MA (US)

(73) Assignee: Medtronic Angiolink, Inc., Santa Rosa, CA (US)

( * ) Notice: Subject to any disclaimer, the term of this patent is extended or adjusted under 35 U.S.C. 154(b) by 1372 days.

This patent is subject to a terminal disclaimer.

(21) Appl. No.: 10/879,955

(22) Filed: Jun. 29, 2004

(65) Prior Publication Data

US 2004/0254591 A1 Dec. 16, 2004

Related U.S. Application Data

(60) Division of application No. 09/884,782, filed on Jun. 19, 2001, now Pat. No. 6,755,842, which is a continuation-in-part of application No. 09/658,786, filed on Sep. 11, 2000, now Pat. No. 6,322,580.

(60) Provisional application No. 60/230,234, filed on Sep. 1, 2000.

(51) Int. Cl.
*A61B 17/04* (2006.01)
(52) U.S. Cl. ...................... 606/213; 606/216
(58) Field of Classification Search ........... 606/198, 606/199, 213, 215, 216, 217, 218
See application file for complete search history.

(56) References Cited

U.S. PATENT DOCUMENTS

| 264,290 | A | 9/1882 | Hogan | |
|---|---|---|---|---|
| 4,821,939 | A | 4/1989 | Green | 227/19 |
| 4,887,601 | A | 12/1989 | Richards | 606/219 |
| 4,955,898 | A | 9/1990 | Matsutani et al. | 606/219 |
| 5,007,921 | A | 4/1991 | Brown | 606/221 |
| 5,026,390 | A | 6/1991 | Brown | 606/221 |
| 5,074,454 | A | 12/1991 | Peters | 227/178 |
| 5,108,421 | A | 4/1992 | Fowler | 606/213 |
| 5,115,958 | A | 5/1992 | Petty | 227/180 |

(Continued)

FOREIGN PATENT DOCUMENTS

EP 0656191 10/1994 .................. 17/128

(Continued)

*Primary Examiner*—Darwin P Erezo

(57) ABSTRACT

An introducer comprises a sheath, a guide rod, at least one wire stabilization guide, and a loop actuation wire for securing and centering a wound opening during a medical procedure (e.g., wherein a transluminal device is utilized) and during closure of the wound. The guide rod is sized to fit within the inside diameter of the sheath. The guide rod has at least one slot along its length for releasably holding the loop actuation wire. One or more wire stabilization guides or elongated members are coupled to the sheath. In one exemplary embodiment, the elongated members may be actuated to form a loop, so that when the sheath is approximated to a wound site, the loop portion is approximated to tissue surrounding the wound site to hold the sheath approximately centered on the wound site. A method for identifying the depth of insertion of a transluminal device into an artery or vein based on the presence of pressurized blood internal to the vessel and the absence of pressurized blood external to the vessel is also provided.

28 Claims, 32 Drawing Sheets

U.S. PATENT DOCUMENTS

| | | | |
|---|---|---|---|
| 5,116,357 A | 5/1992 | Eberbach | 606/213 |
| 5,122,156 A | 6/1992 | Granger et al. | 606/219 |
| 5,129,570 A | 7/1992 | Schulze et al. | 227/19 |
| 5,141,515 A | 8/1992 | Eberbach | 606/151 |
| 5,158,567 A | 10/1992 | Green | 606/219 |
| 5,170,926 A | 12/1992 | Ruckdeschel et al. | 227/177 |
| 5,192,302 A | 3/1993 | Kensye et al. | 606/213 |
| 5,222,974 A | 6/1993 | Kensey et al. | 606/213 |
| 5,234,447 A | 8/1993 | Kaster et al. | 606/153 |
| 5,251,801 A | 10/1993 | Ruckdeschel et al. | 227/177 |
| 5,275,610 A * | 1/1994 | Eberbach | 606/198 |
| 5,297,714 A | 3/1994 | Kramer | 227/175 |
| 5,324,306 A | 6/1994 | Makower et al. | 606/213 |
| 5,366,479 A | 11/1994 | McGarry et al. | 606/219 |
| 5,392,978 A | 2/1995 | Velez et al. | 227/177 |
| 5,397,310 A | 3/1995 | Chu et al. | 604/158 |
| 5,411,520 A | 5/1995 | Nash et al. | 606/213 |
| 5,413,584 A | 5/1995 | Schulze | 606/219 |
| 5,415,334 A | 5/1995 | Williamson | 227/178 |
| 5,423,857 A | 6/1995 | Rosenman et al. | 606/219 |
| 5,433,727 A | 7/1995 | Sideris | 606/213 |
| 5,441,517 A | 8/1995 | Kensey et al. | 606/213 |
| 5,465,895 A | 11/1995 | Knodel et al. | 227/176 |
| 5,476,469 A | 12/1995 | Hathaway et al. | 606/144 |
| 5,478,354 A | 12/1995 | Tovey et al. | 606/219 |
| 5,496,332 A | 3/1996 | Sierra et al. | 606/139 |
| 5,507,776 A | 4/1996 | Hempel | 606/219 |
| 5,540,375 A | 7/1996 | Bolanos et al. | 227/178.1 |
| 5,549,633 A | 8/1996 | Evans et al. | 606/139 |
| 5,584,856 A | 12/1996 | Jameel et al. | 606/220 |
| 5,613,974 A | 3/1997 | Andreas et al. | 606/144 |
| 5,630,541 A | 5/1997 | Williamson, IV et al. | 227/178.1 |
| 5,645,567 A | 7/1997 | Crainich | 606/219 |
| 5,676,689 A | 10/1997 | Kensey et al. | 606/213 |
| 5,681,334 A | 10/1997 | Evans et al. | 606/148 |
| 5,690,269 A | 11/1997 | Bolanos et al. | 227/176.1 |
| 5,695,504 A | 12/1997 | Gifford, III et al. | 606/153 |
| 5,709,335 A | 1/1998 | Heck et al. | 227/176.1 |
| 5,738,474 A | 4/1998 | Blewett | 411/473 |
| 5,779,132 A | 7/1998 | Knodel et al. | 227/176.1 |
| 5,810,846 A | 9/1998 | Virnich et al. | 606/142 |
| 5,871,135 A | 2/1999 | Williamson, IV et al. | 227/178.1 |
| 5,902,274 A * | 5/1999 | Yamamoto et al. | 604/164.12 |
| 5,919,207 A | 7/1999 | Taheri | 606/219 |
| 5,941,890 A | 8/1999 | Voegele et al. | 606/151 |
| 6,004,341 A | 12/1999 | Zhu et al. | 606/198 |
| 6,015,417 A | 1/2000 | Reynolds, Jr. | 606/151 |
| 6,022,372 A | 2/2000 | Kontos | 606/219 |
| 6,045,569 A | 4/2000 | Kensey et al. | 606/213 |
| 6,048,357 A | 4/2000 | Kontos | 606/213 |
| 6,090,130 A | 7/2000 | Nash et al. | 606/213 |
| 6,149,658 A | 11/2000 | Gardiner et al. | 606/139 |
| 6,159,232 A | 12/2000 | Nowakowski | 606/213 |
| 6,187,025 B1 * | 2/2001 | Machek | 606/200 |
| 6,197,042 B1 | 3/2001 | Ginn et al. | 606/213 |
| 6,206,893 B1 | 3/2001 | Klein et al. | 606/144 |
| 6,231,573 B1 * | 5/2001 | Amor et al. | 606/49 |
| 6,254,609 B1 * | 7/2001 | Vrba et al. | 606/108 |
| 6,368,341 B1 * | 4/2002 | Abrahamson | 606/213 |
| 6,461,364 B1 | 10/2002 | Ginn et al. | 606/142 |
| 7,198,631 B2 * | 4/2007 | Kanner et al. | 606/139 |
| 2002/0026208 A1 | 2/2002 | Roe et al. | 606/190 |

FOREIGN PATENT DOCUMENTS

| | | | | |
|---|---|---|---|---|
| WO | WO 02/19920 A1 | 3/2002 | | 17/64 |
| WO | WO 02/19922 A1 | 3/2002 | | 17/68 |

* cited by examiner

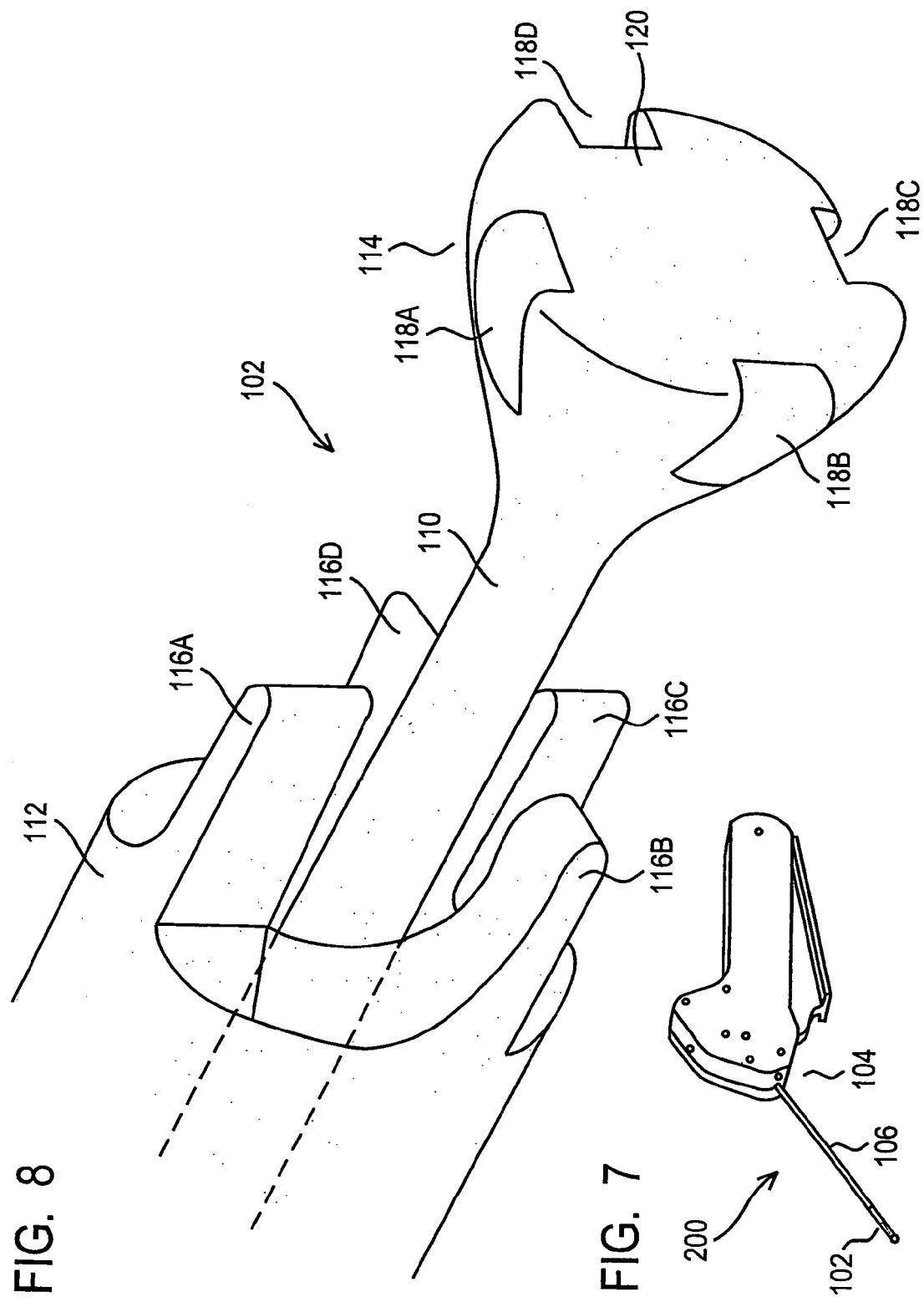

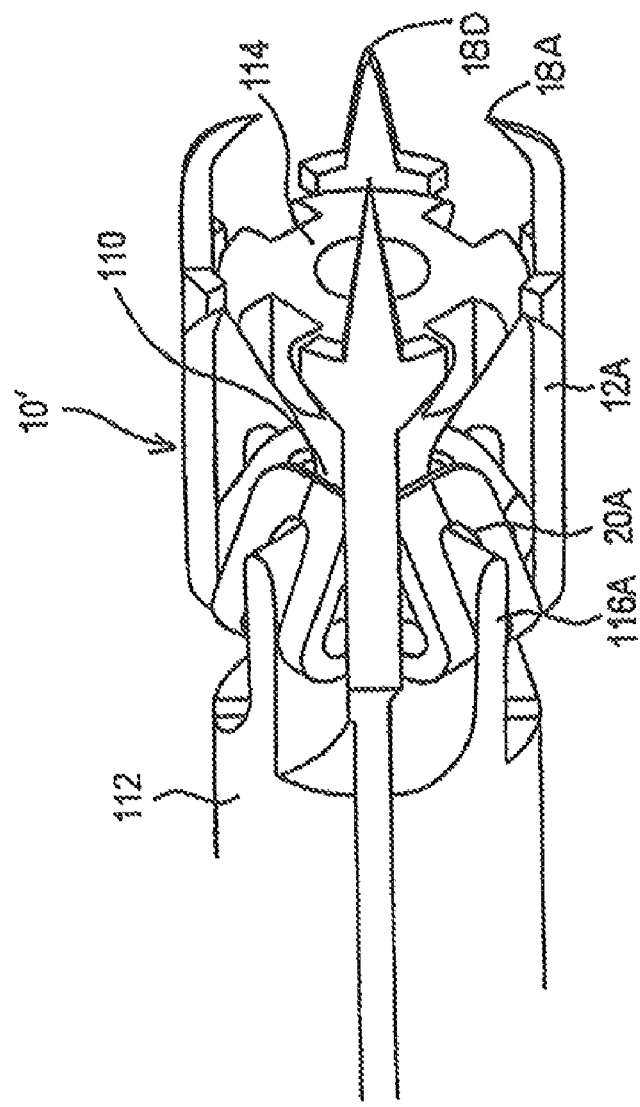
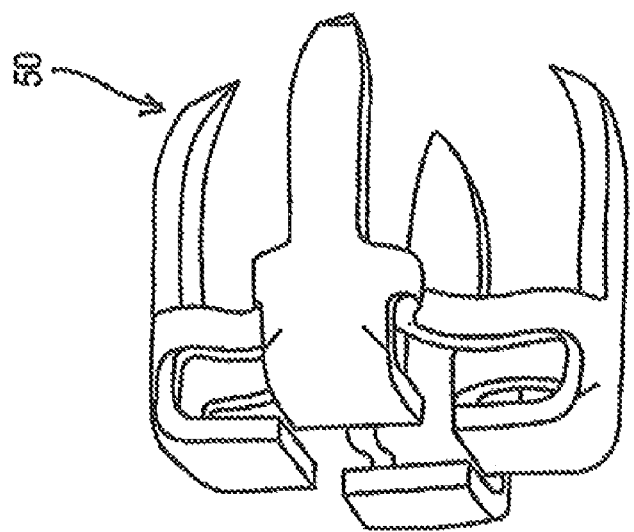
FIG. 9A
FIG. 9B

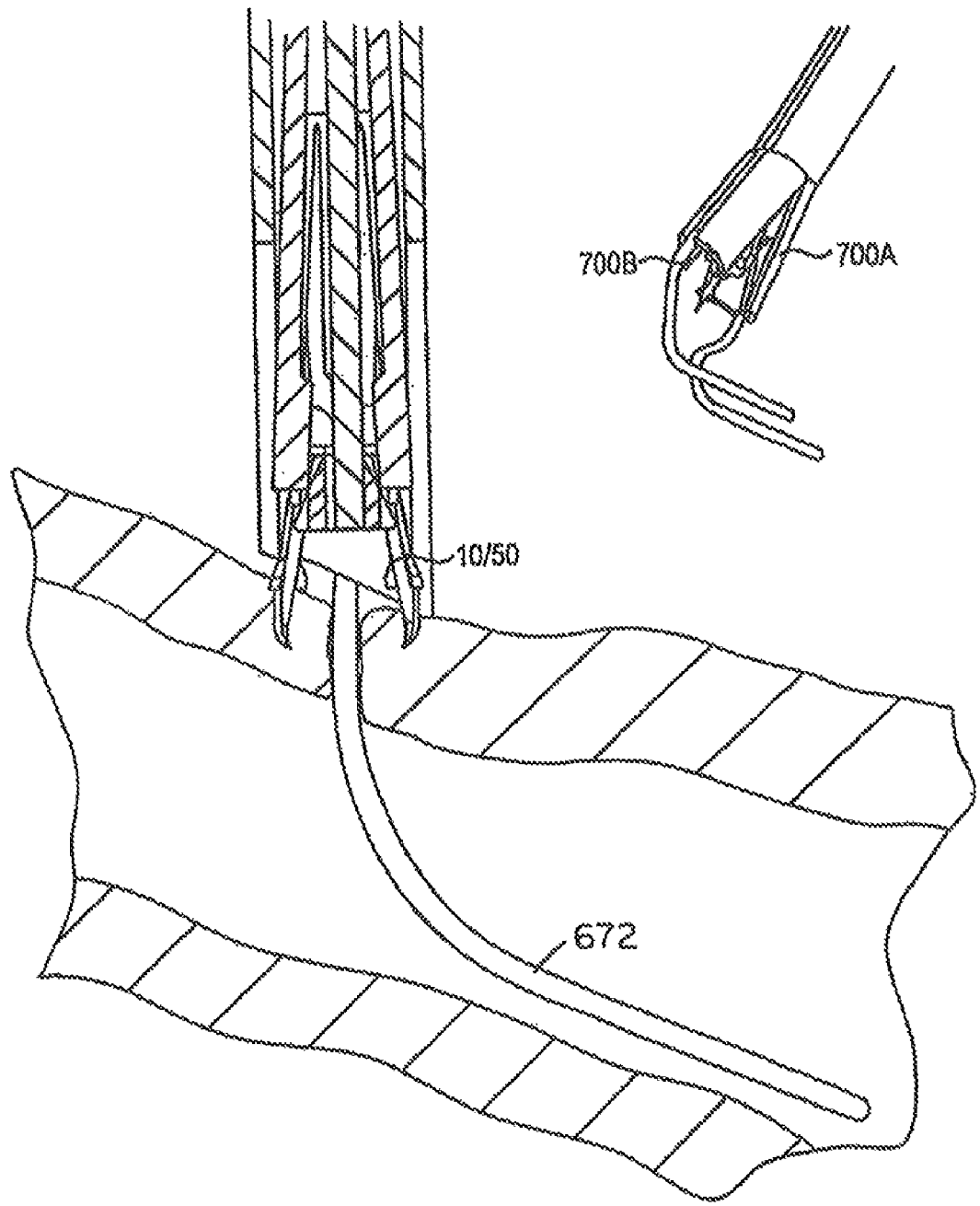

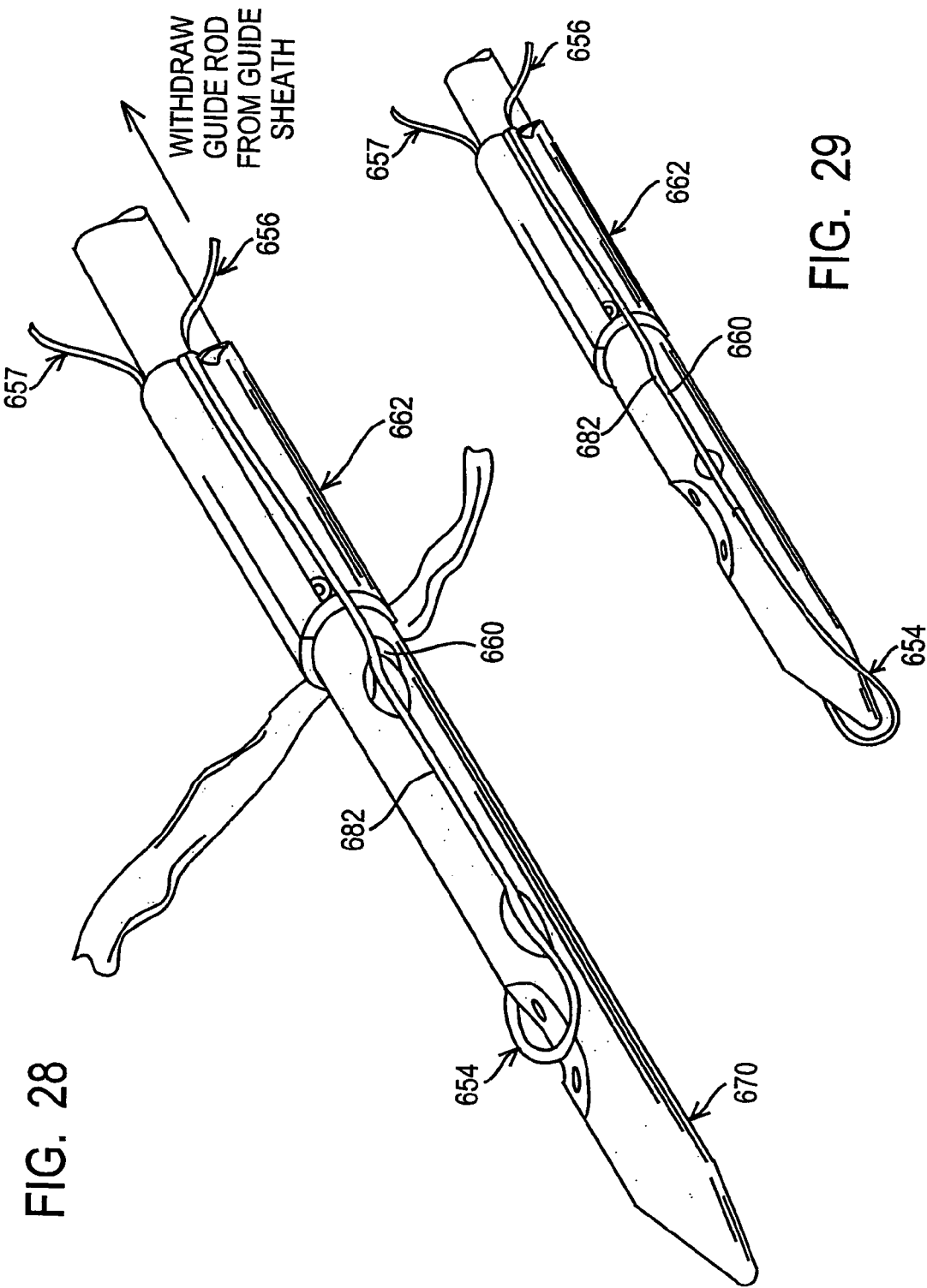

FIG. 39
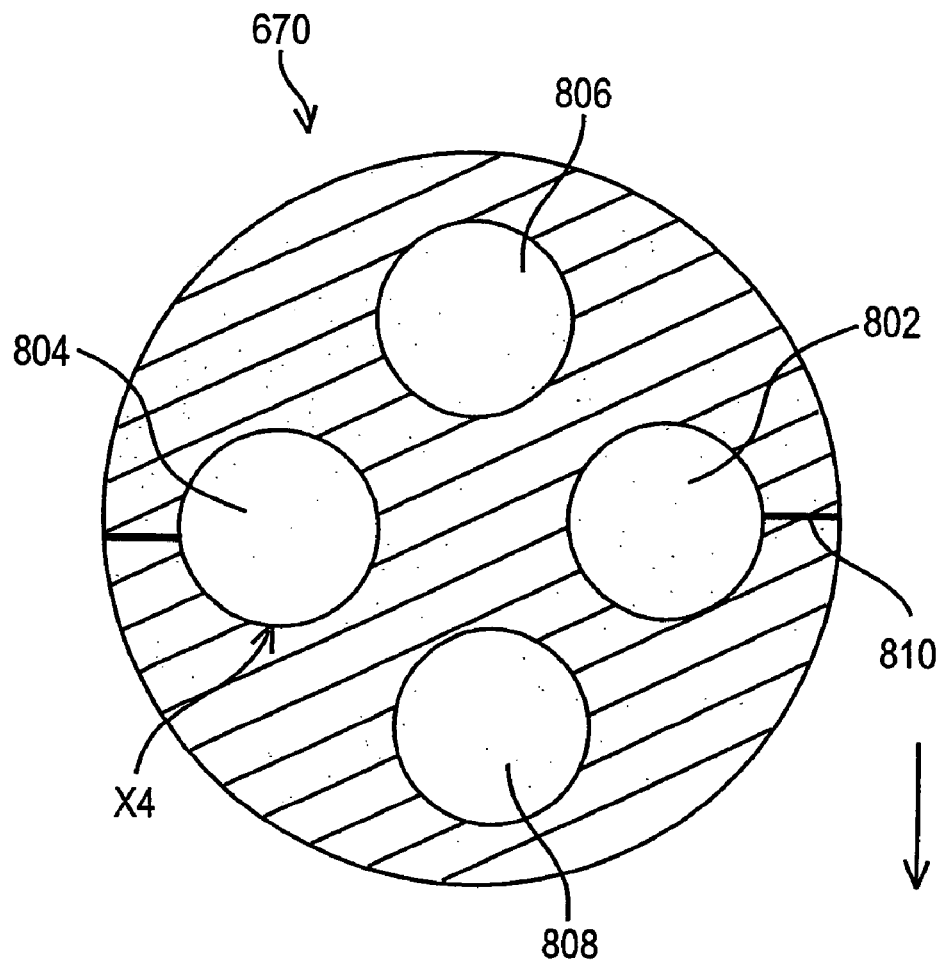
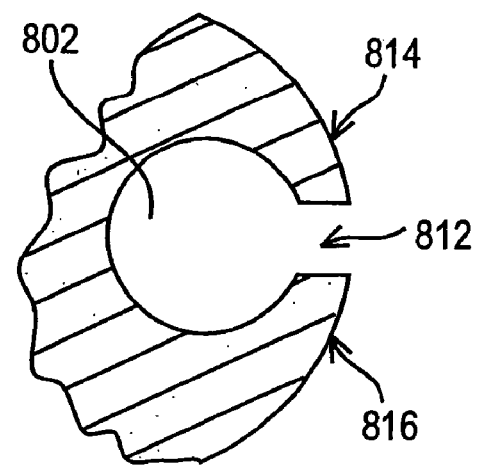
FIG. 39A

ADVANCED WOUND SITE MANAGEMENT SYSTEMS AND METHODS

CROSS-REFERENCE TO RELATED APPLICATION

This application is a divisional of U.S. patent application Ser. No. 09/884,782, filed Jun. 19, 2001, now U.S. Pat. No. 6,755,842, which is a continuation-in-part of U.S. patent application Ser. No. 09/658,786, filed Sep. 11, 2000, now U.S. Pat. No. 6,322,580, which claims benefit of U.S. provisional application Ser. No. 60/230,234 filed Sep. 1, 2000. The entire disclosures of all of the above-identified applications are incorporated herein by reference.

BACKGROUND OF THE INVENTION

1. Field of the Invention

The present invention relates to a wound site management, for use during and after an invasive medical procedure. More specifically, the present invention relates to wound site management techniques and methodology for diagnostic and interventional procedures occurring at a wound site, for example, a puncture made in the wall of an artery or vein during a medical procedure. The puncture may be the result of a catheter-based intervention, although any puncture is contemplated, accidental or intentional. The present invention has particular utility for use in and around the femoral, radial, and brachial arteries after coronary/cardiac procedures. Other utilities include soft-tissue anchoring, tendon and artery joining, meniscal repair, thoracic lung closure, heart repair, endoscopic procedures, esophageal repair, laparoscopy, skin/epidermal wound closure and general tissue closure.

2. Description of Related Art

Catheters/catheterization procedures are well known, and typically involve insertions through the femoral artery for diagnosis or to treat cardiovascular and/or peripheral vascular diseases. After a diagnostic or interventional catheterization, the puncture formed by the catheter must be closed. The puncture opening in the artery typically ranges from 5 F for a diagnostic procedure to 6-10 F for an interventional procedure. Traditionally, intense pressure has been applied to the puncture site for at least 30-45 minutes after removal of the catheter. Other approaches include a thrombotic or collagen plug, and/or other suturing methodology for sealing the puncture. Patients who have had a femoral puncture are then required to remain at bed rest, essentially motionless and often with a heavy sandbag placed on their upper legs, for several hours to ensure that the bleeding has stopped. This traditional method of hemostasis following femoral artery access has many inadequacies. When a blockage is removed during a procedure, the patient quickly feels better and they often have more energy than they have had in years, but they must remain motionless for several hours. The weight of the sandbag on the femoral artery often causes the lower leg to tingle or go numb. The recovery time from the medical procedure may be as little as ½ hour, but the recovery time from the wound can exceed 24 hours. The longer the recovery time, the more expensive the procedure becomes, the greater the patient discomfort, and the greater the risk of complications.

SUMMARY OF THE INVENTION

The invention relates to wound site management systems and techniques and, particularly, to those aspects relating to introducing a guide for a wound closure means (e.g., suture, staple, adhesive) to a wound site while configuring the wound site to receive the wound closure means. The invention includes a guide, such as a sheath, for guiding the wound closure means. One or more stabilizing elements are carried by and extend distally beyond the distal end of the sheath to engage tissue about the wound site in a manner that causes opposing portions of the tissue about the wound site to be drawn together in readiness for application of the wound closure means. The stabilizers may be configured in a variety of arrangements and may be actuated resiliently or by wires controllable from the proximal end of the device.

BRIEF DESCRIPTION OF THE DRAWINGS

It will be appreciated by those skilled in the art that although the following Detailed Description will proceed with reference being made to preferred embodiments the present invention is not intended to be limited to these preferred embodiments. Other features and advantages of the present invention will become apparent as the following Detailed Description proceeds, and upon reference to the Drawings, wherein like numerals depict like parts, and wherein:

FIG. 3A depicts an isometric view of alternative staple of the embodiment of FIGS. 1-3;

FIG. 7 depicts one embodiment of the stapler of the present invention;

FIG. 8 is an isometric view of the distal tip of the stapler of FIG. 7 adapted to hold and deploy the staple of FIGS. 1-6;

FIGS. 9A-11B are isometric views of the cooperative movement of the distal tip of the stapler and the staple of the present invention;

FIGS. 18-26 depict various views of procedural embodiments of the present invention, including FIG. 20 depicting one embodiment of the introducer of the present invention;

FIGS. 27-34, 39 and 39A are isometric views of one exemplary embodiment of an introducer of the present invention;

DETAILED DESCRIPTION OF THE INVENTION

Tissue Staple

In one aspect of the present invention, a staple is provided to close a tissue wound after a medical procedure. Although the preferred use of the staple of the present invention is to close an artery or vein following a diagnostic or interventional procedure, it should be recognized at the outset that the staple may be used for general tissue repair, not just limited to vascular repair. It will be appreciated throughout the following description that the staple of the present invention can be formed of any biocompatible and/or bioabsorbable materials, including, for example, Titanium (and Titanium alloys), stainless steel, polymeric materials (synthetic and/or natural), ceramic, etc. It will also be apparent from the following description that the staple of the present invention is preferably formed of a deformable material (such as those listed above) that undergoes plastic deformation (i.e., deformation with negligible elastic component.) As a general overview, the staple of the present invention undergoes two positions of deformation: a first position to extend the distal ends of the prongs of the staple outwardly to grab a greater amount of tissue (and also to grab tissue away from the wound locus), and a second position to move the prongs inwardly to close the wound.

Figure 1:
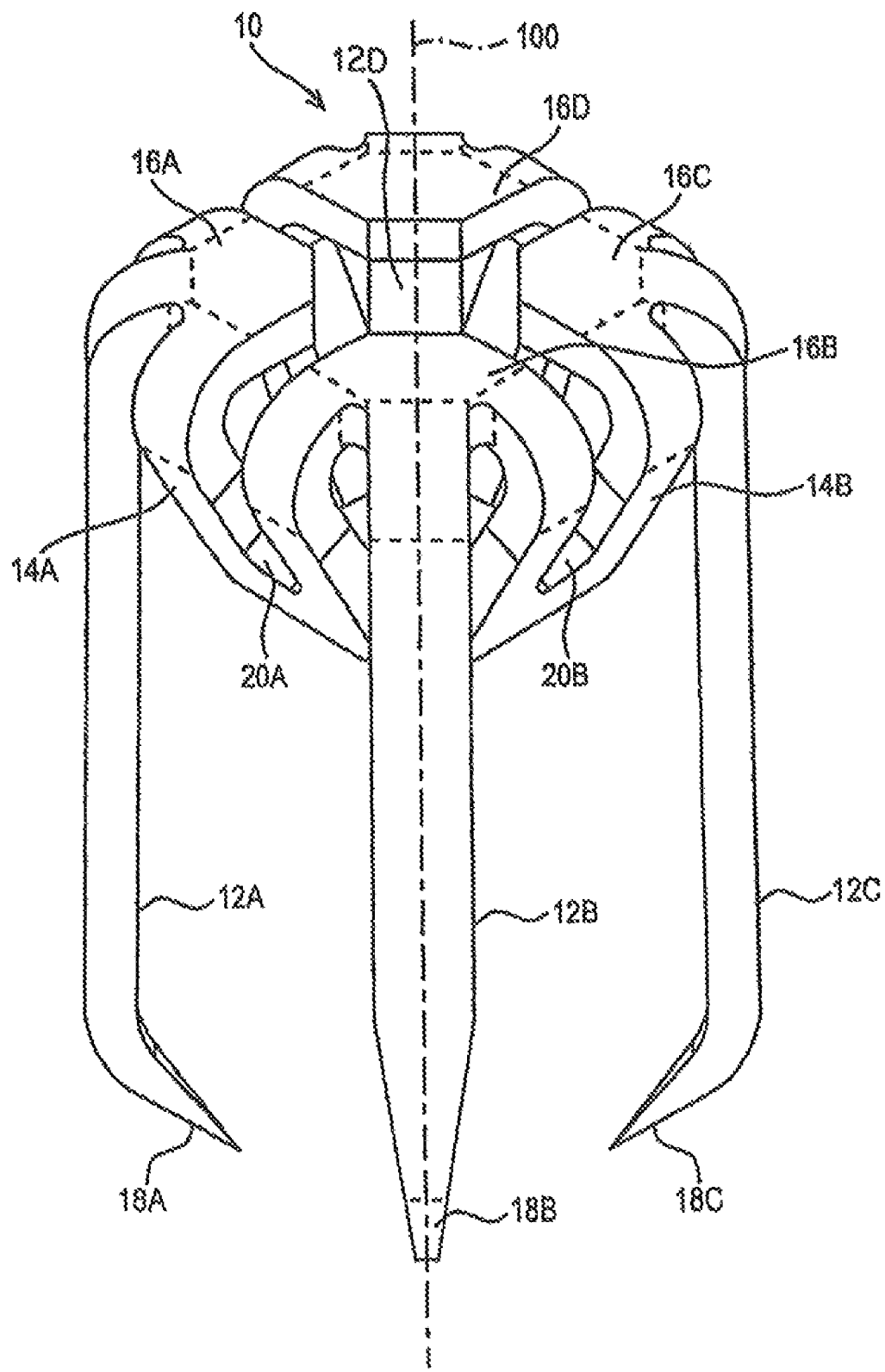
FIGS. 1-3 are isometric views of one embodiment of the staple of the present invention in formed, opened and deployed positions, respectively.
Figure 2:
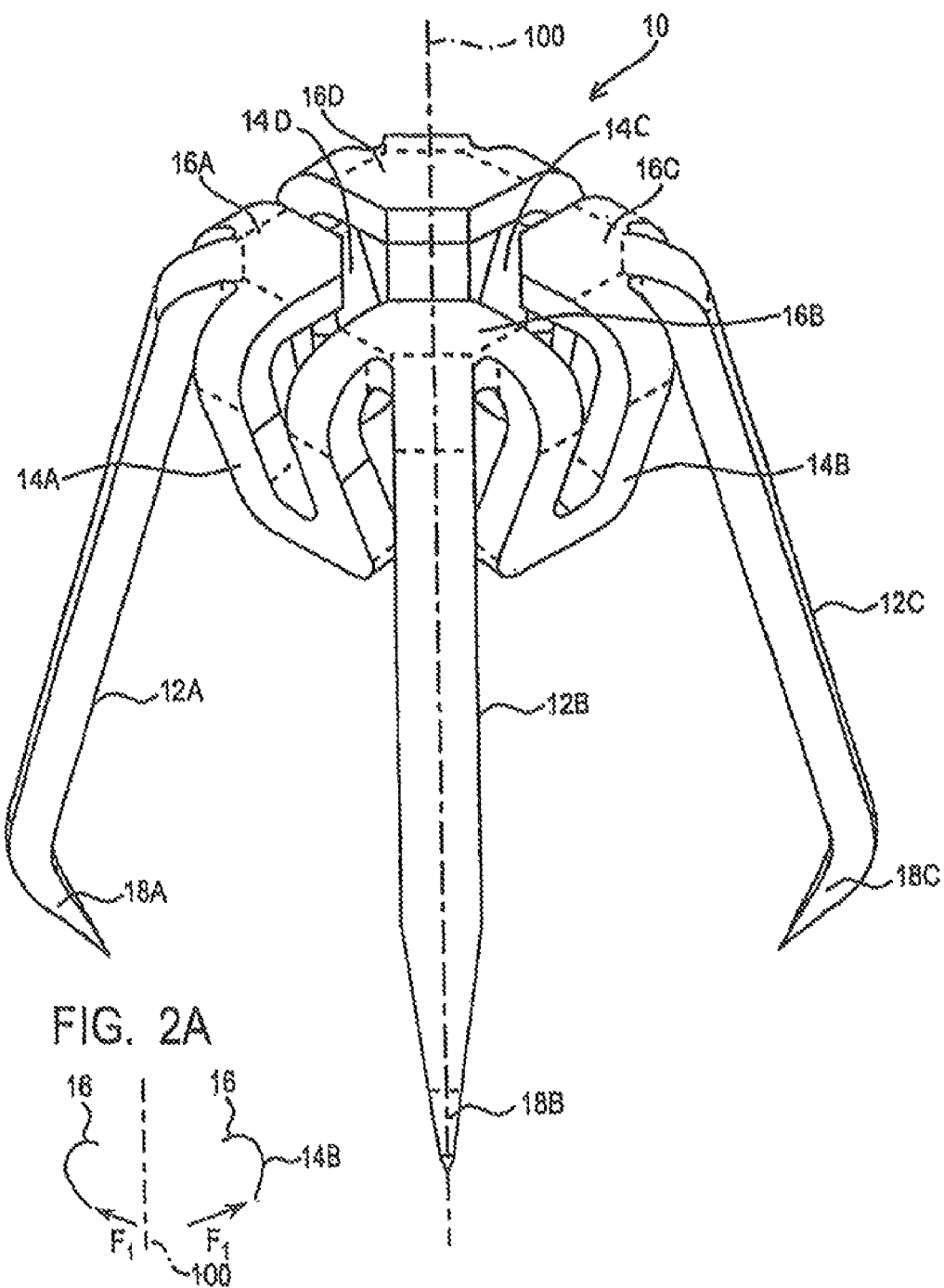
Figure 3:
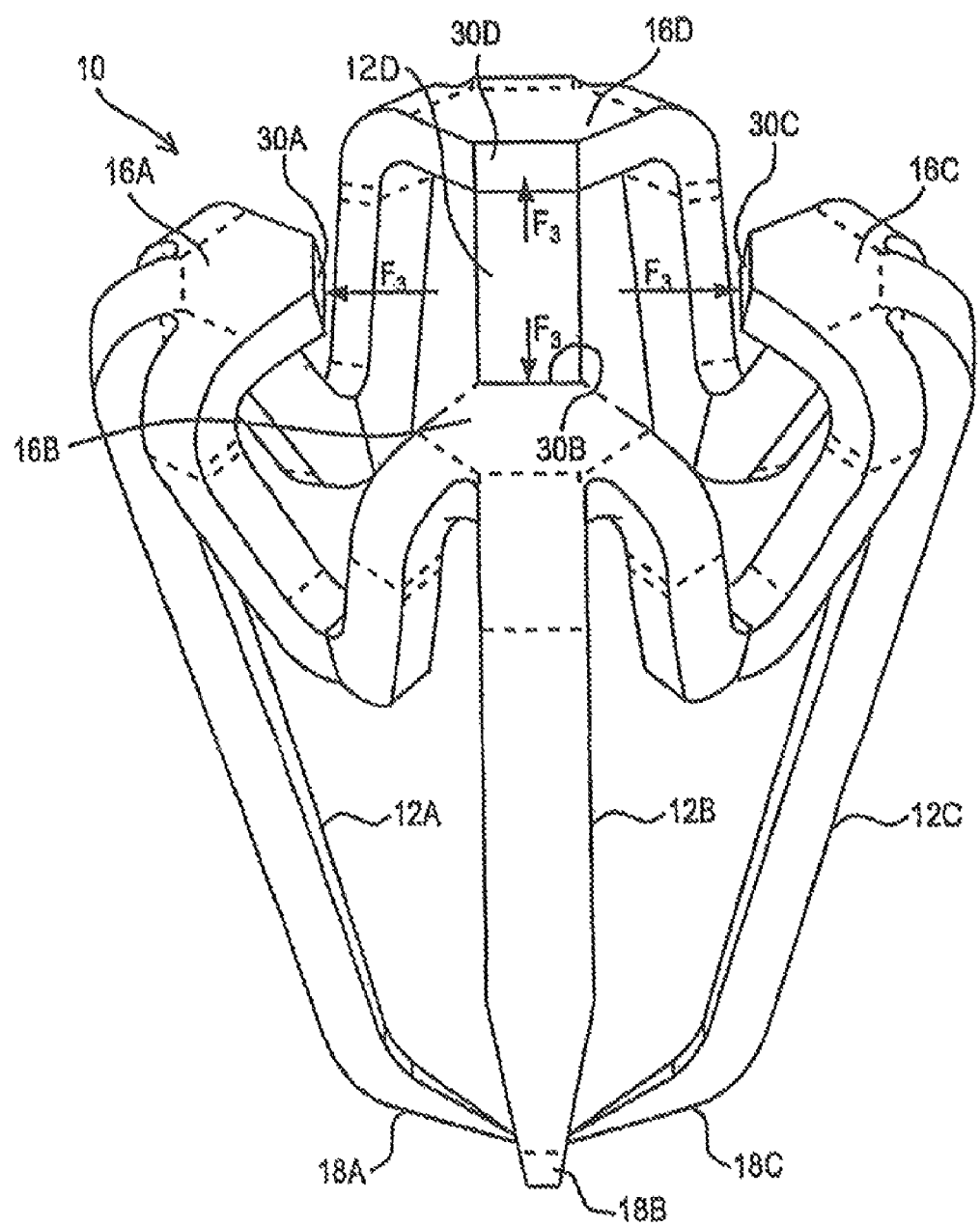

FIGS. 1, 2 and 3 depict one embodiment of staple 10 of the present invention. FIG. 1 is the staple in it's formed position, FIG. 2 is the staple just prior to deployment into tissue with the prongs extended outwardly, and FIG. 3 is the staple closed around tissue. The staple 10 of this embodiment comprises a plurality of prongs 12A-12D and a plurality of tabs 14A-14D, arranged about a centerline axis 100. Common portions, or shoulders 16A-16D are formed where the tabs meet the prongs. Each shoulder is common to both the prong and the tab and is generally defined by a relatively flat portion generally orthogonal to the centerline axis. Shoulders 16A-16D may be viewed as an extension of each prong, bent inwardly toward the centerline axis. Each of these features of the staple 10 of this embodiment is detailed below.

In the formed position (FIG. 1), prongs 12A-12D extend generally parallel to central axis 100, as shown. At the distal end of each prong, tapered points 18A-18D is formed to extend inwardly toward the centerline axis 100. At the proximal end, shoulders 16A-16D meet at prongs 12A-12D, respectively. Tabs 14A-14D are generally U-shaped, and are formed between each prong. The proximal portions of each tab are joined at consecutive shoulders, as shown. Each proximal portion of the U (i.e., each "leg" of the U-shape tab) extends first generally outward from the shoulder, and second bends inwardly and distally toward centerline axis 100, connecting together nearest the centerline axis to form the U shape. The U-shape defines slots 20A-20D within each tab having a base positioned at the bottom thereof.

Referring specifically to FIG. 2, the staple 10 is deformed so that prongs 12A-12D extend outwardly from the centerline axis, prior to deployment into tissue. It is advantageous to extend the prongs outwardly as shown so as to grasp a large portion of the tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 2, a force $F_1$ is applied to tabs 14A-14D, as shown in relief in FIG. 2A. Force $F_1$ is generally outward (from the centerline axis) and proximal to the top of the staple, as shown in relief in FIG. 2A. This force causes the tabs to move outward from the centerline axis 100. The outward movement of the tabs causes the shoulder portions to pivot roughly about the juncture between the shoulder and the prong (i.e., at the outer portion of the shoulder), causing the inner portions of the shoulders to move inwardly toward the centerline axis and distally. Since the prongs are attached to the outer portion of the shoulders, the movement of the shoulders in this manner causes the prongs to move outwardly. Thus, the cross-sectional diameter of the staple gets larger at the distal end (with respect to the cross-sectional diameter of the formed staple of FIG. 1). Note that the movement of the prongs is generally greater at the distal portions thereof than at the proximal portions thereof. In other words, movement of the prongs as shown in FIG. 2 is pivoted from the shoulder, thus producing a staple with outwardly extending prongs. For completeness, it should be noted that a holding force may be applied downwardly (i.e., substantially parallel to the centerline axis) against the base of the slots 20A-20D to hold the staple in place. Also, it is preferred that these forces are simultaneously applied to each tab of the staple to produce uniform deformation of each prong of the staple. As mentioned above, it is preferable that the plastic deformation of the staple is semi-permanent, so that the staple does not tend to return to the shape depicted in FIG. 1 (i.e., non-elastic deformation). Deformation of the staple into this position will be described in greater detail below in reference to the preferred stapler device of the present invention.

FIG. 3 depicts the staple 10 in a closed position. The closed position, as stated herein generally means that the prongs of the staple are moved inwardly toward each other. Although FIG. 3 depicts the tapered tip portions of the prongs meeting generally in the vicinity of the centerline axis, however, it should be understood that the term "closed" or "deployed" as used in reference to the staple need not necessarily mean this precise configuration. It may be required (or desirable) for some procedures to move the prongs inwardly toward each other to a greater or lesser extent than as depicted in FIG. 3. To draw the staple into the closed position depicted in this Figure, a force $F_3$ is applied to the inner surfaces 30A-30D of the shoulders. This force is generally orthogonal to the centerline axis, and the angle between each force approximates the angle between the inner surfaces 30A-30D (which, in the staple of this embodiment is approximately 90 degrees). This force causes the slots 20A-20D to spread apart and urges the shoulders outwardly. Movement in this manner also causes the shoulders to move outwardly and proximally. Proximal movement of the shoulders causes the prongs to move toward each other. Opposite to the movement of FIG. 2, deformation shown in FIG. 3 results in an expanded cross-sectional diameter of the proximal end of staple, and a diminished cross-sectional diameter of the distal end of the staple (with respect to the formed staple of FIG. 1 and the deformed staple of FIG. 2). Again, deformation of the staple 10 into this position will be described in greater detail below in reference to the preferred stapler device of the present invention.

For certain tissue application, it may be desirable that the staple of the present invention is deployed into tissue such that the prongs do not fully pierce through the tissue, but rather grasp and hold the tissue together. For example, for vascular closure applications it may be desirable that the tissue piercing tapered ends not enter the bloodstream, but rather pierce into the tissue and stop short of piercing through the tissue wall. To that end, and referring to FIG. 3A, the staple 10' of the present invention can be adapted with tissue stops 32A-32D. Preferably, tissue stops 32A-32D are located along the length of each prong, and positioned from the distal tip of the prong to permit the tapered ends to pierce tissue, but not pierce all the way through the tissue. Accordingly, the position of the stops 32A-32D along the length of the prongs is selected to facilitate tissue grabbing (but not complete tissue piercing) and can vary from application to application.

Figure 4:
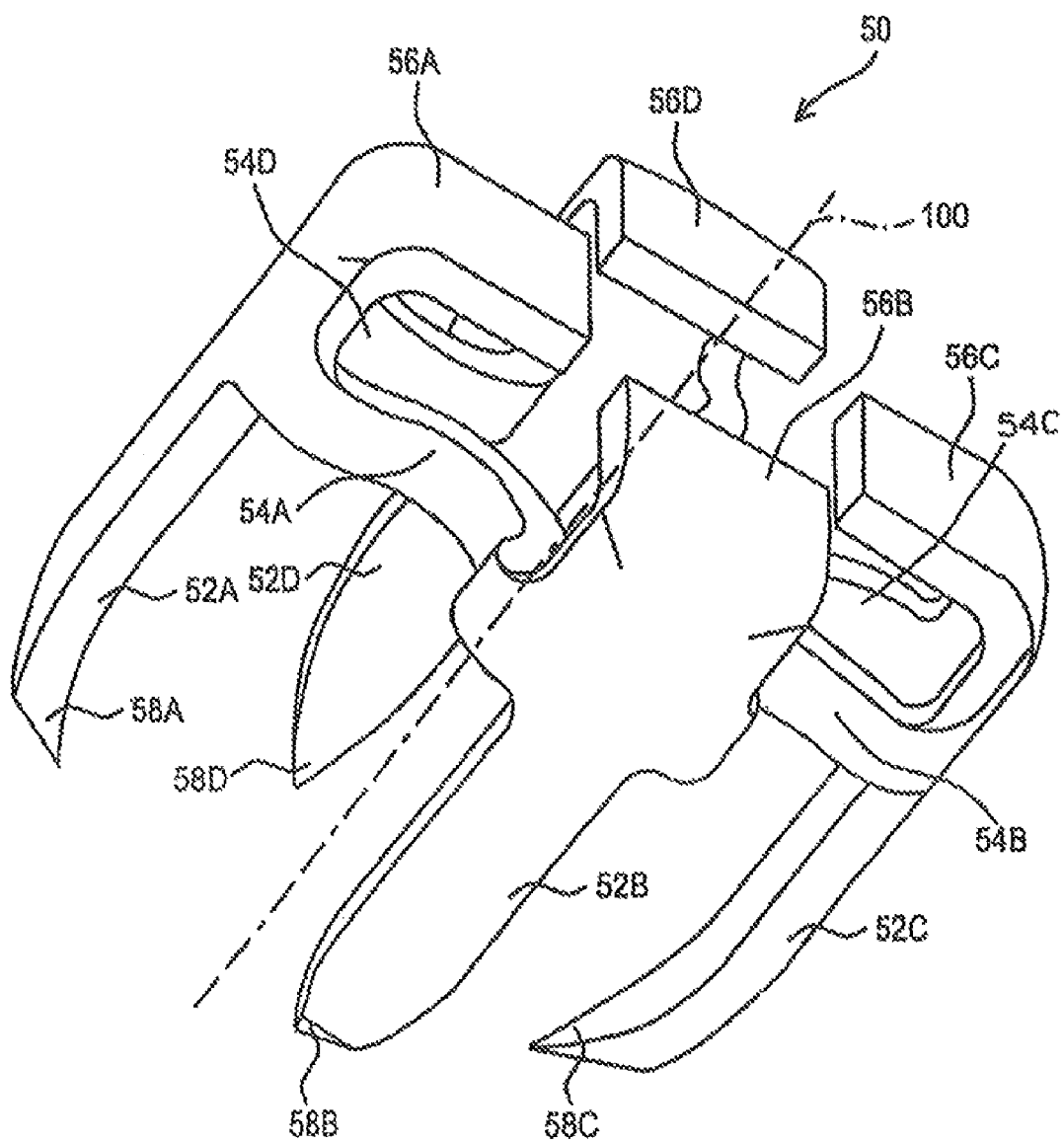
FIGS. 4-6 are isometric views of another embodiment of the staple of the present invention in formed, opened and deployed positions, respectively.
Figure 5:
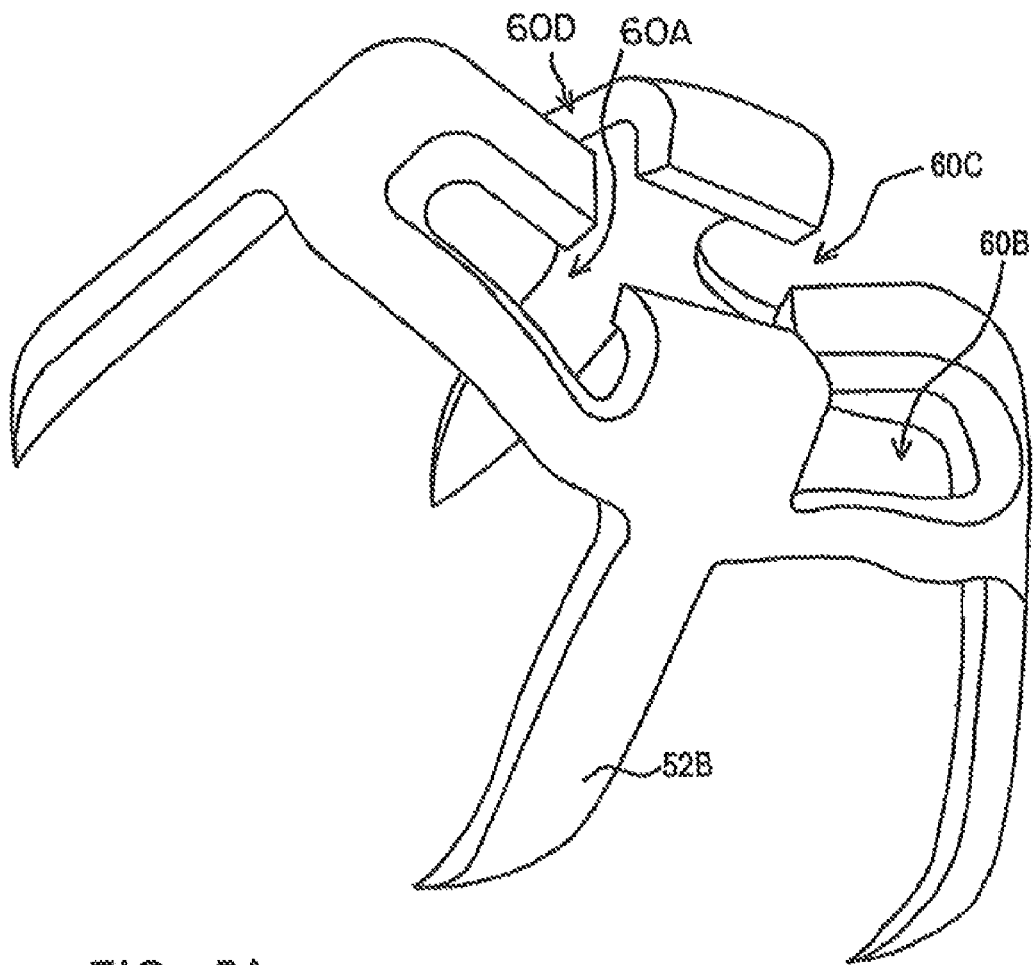
Figure 6:
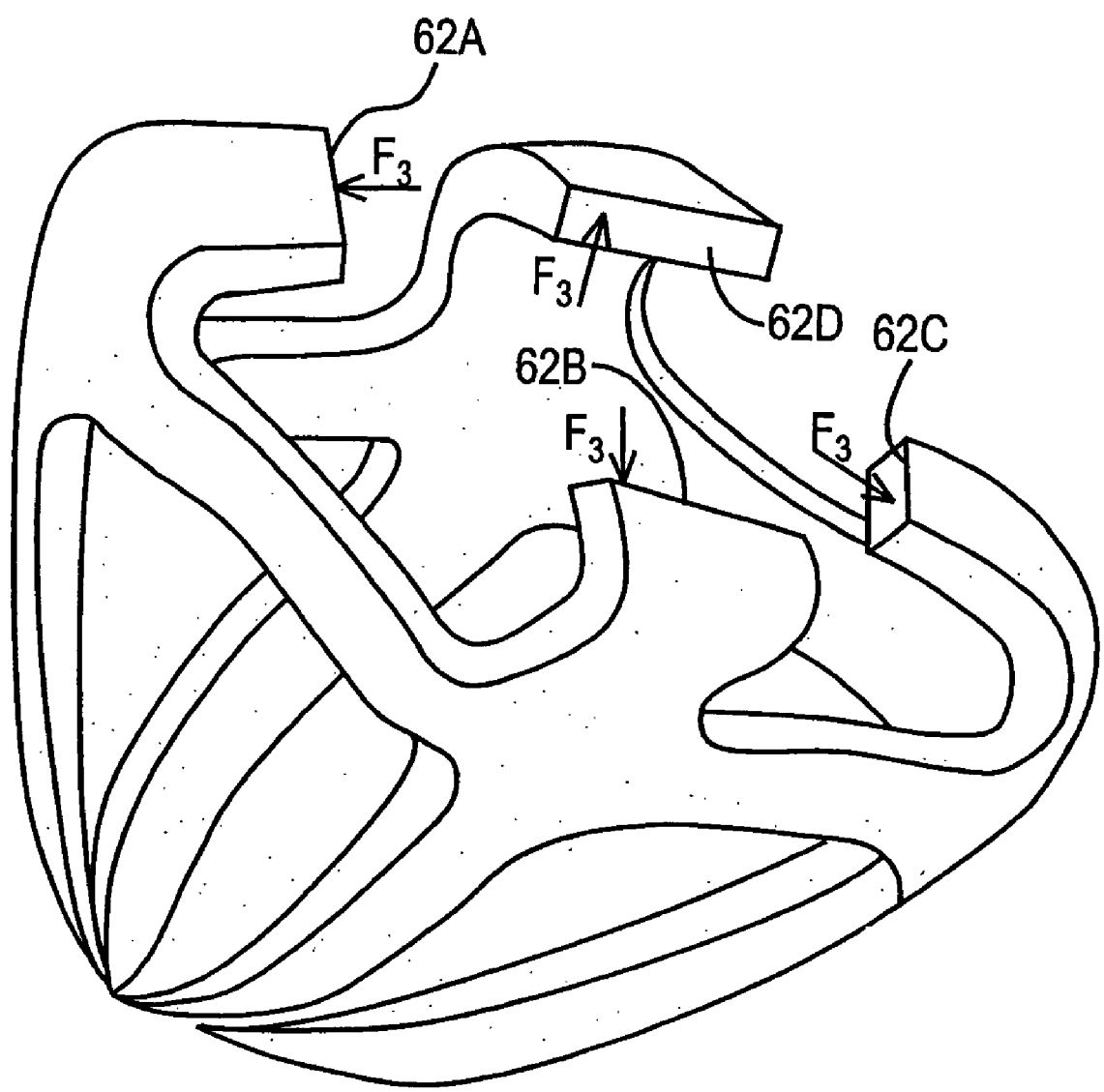

FIGS. 4-6 depict another embodiment of a staple 50 of the present invention. FIG. 4 is the staple in it's formed position, FIG. 5 is the staple just prior to deployment into tissue with the prongs extended outwardly, and FIG. 6 is the staple closed around tissue. Similar to the first embodiment, the staple 50 of this embodiment comprises a plurality of prongs 52A-52D arranged about a centerline axis 100. A shoulder 56A-56D is provided and is generally defined by a relatively flat surface, generally orthogonal to centerline axis. Shoulders 56A-56D may be viewed as an extension of each prong, bent inwardly toward the centerline axis. In this embodiment, webs 54A-54D are connected to and between each prong, and are formed to extend inwardly from each prong toward the centerline axis, creating a U shape generally orthogonal to the centerline axis (as opposed to the previous embodiment in which the U-shaped tab is positioned generally parallel to the centerline axis). Each of the features of the staple 50 of this embodiment is detailed below.

In the formed position (FIG. 4), prongs 52A-52D extend generally parallel to central axis 100, as shown. At the distal end of each prong, tapered points 58A-58D are formed to extend inwardly toward the centerline axis 100. At the proximal end, shoulders 56A-56D meet at prongs 52A-52D, respectively. Web portions (webs) 54A-54D are generally U-shaped, and are formed between each prong extending inwardly toward the centerline axis. As shown, webs connect the prongs at a position distal to the shoulders. The precise position of the webs is determined by the desired extent to which the prongs are extended outwardly, and the extent to which the web curves inward toward the centerline axis. The space between the shoulders and the web portions defines a slot 60A-60D.

Figure 5A:
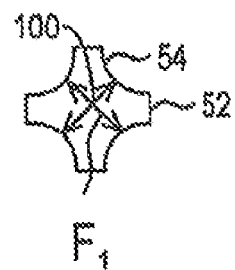

Referring specifically to FIG. 5, the staple 50 is deformed so that prongs 52A-52D extend outwardly from the centerline axis, prior to deployment into tissue. As with the previous embodiment, it is advantageous to extend the prongs outwardly as shown so as to grasp a large portion of tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 5, a force $F_1$ is applied to webs 54A-54D, as shown in relief in FIG. 5A. Force $F_1$ is generally outward from the centerline axis and causes the webs to deform outwardly, i.e. straightening the bend of the web by moving the centermost point of the web outwardly. By deformation of the web portions in this manner, the prongs move outwardly. Thus, the cross-sectional diameter of the staple gets larger at the distal end (with respect to the cross-sectional diameter of the formed staple of FIG. 4). Note that the movement of the prongs is generally greater at the distal portions thereof than at the proximal portions thereof, thus producing a staple with outwardly extending prongs. For completeness, it should be noted that a holding force may be applied downwardly (i.e., substantially parallel to the centerline axis) against the top of the webs in slots 60A-60D to hold the staple in place. Also, it is preferred that these forces are simultaneously applied to each web of the staple to produce uniform deformation of each prong of the staple. As mentioned above, it is preferable that the deformation of the staple is plastic, so that the staple does not tend to return to the shape depicted in FIG. 4. Deformation of the staple into this position will be described in greater detail below in reference to the preferred stapler device of the present invention.

FIG. 6 depicts the staple 50 in a closed or deployed position. The closed position, as stated herein generally means that the prongs of the staple are moved inwardly toward each other. To draw the staple into the closed position depicted in this Figure, a force $F_3$ is applied to the inner surfaces 62A-62D of the shoulders. This force is generally orthogonal to the centerline axis, and the angle between each force approximates the angle between the inner surfaces 62A-62D about the centerline axis (which, in the staple of this embodiment is approximately 90 degrees). This force urges the shoulders outwardly. Note that shoulders can only extend outwardly as far as the web portions will permit. Outward movement of the shoulders causes the prongs to move toward each other, since, there is a general pivot about the web portions. Opposite to the movement of FIG. 5, deformation shown in FIG. 6 results in an expanded cross-sectional diameter of the proximal end of staple, and a diminished cross-sectional diameter of the distal end of the staple (with respect to the formed staple of FIG. 4 and the deformed staple of FIG. 5). Again, deformation of the staple 50 into this position will be described in greater detail below in reference to the preferred stapler device of the present invention.

In either embodiment described above, it should be evident that although the Figures depict four each of the prongs, tabs and shoulders, this should be only be considered exemplary. It may be desirable to adapt the staple 10 or the staple 50 with more or fewer prongs, tabs and shoulders for a given application. Also, it is not necessary that each prong is the same length, or that each prong has the same overall dimensions. In alternative embodiments, the entire staple, or selected portions thereof can be alternatively fashioned from an elastic or shape memory (e.g., nitinol, and/or other elastic materials, including for example temperature dependant shape memory materials) material thereby permitting elastic deformation from the a static closed position to an expanded position and then elastically close about the wound. Also, the embodiment of FIGS. 4-6 can be adapted with a tissue stop positioned along the length of the prong, as shown in FIG. 3A.

Stapler Device

Another aspect of the present invention is a stapler device to deploy the staple 10 of FIGS. 1-3, the staple 10' of FIG. 3A, and the staple 50 of FIGS. 4-6. As a general overview, the stapler of the present invention includes a distal tip for holding and deploying a staple, and an actuator mechanism to cause a staple, or at least the tissue piercing portions of a staple, to expand outwardly and then close about a wound. The stapler of the present invention facilitates one object of the present invention to ensure that the staple closes a greater amount of tissue as compared with conventional stapling mechanisms. The following description will detail various exemplary mechanisms to accomplish this goal, but it should be recognized that numerous alternatives will be readily apparent to those skilled in the art, and all such alternatives are to accomplish these objectives are deemed within the scope of the present invention.

FIG. 7 depicts an isometric view of one embodiment of a stapling device 200 of the present invention. The device generally includes an actuation mechanism 104 and a distal tip 102. FIG. 8 is a more detailed view of the distal tip 102 of the stapler device 200. The distal tip preferably comprises an inner rod member 110 slidable within an outer sleeve 112. Rod 110 includes a flared or mandrel portion 114. Mandrel 114 also includes slots 118A-118D, which in use are aligned with fingers 116A-116D. Fingers 116A-116D mate with slots 20A-20D and 60A-60D of the staple 10 and 50, respectively, Preferably, rod 110 is removable for staple attachment thereto, where a staple is positioned between the mandrel and the sleeve. The mandrel, as will be described below, is responsible for the forces generated on the staple.

Figure 10B:
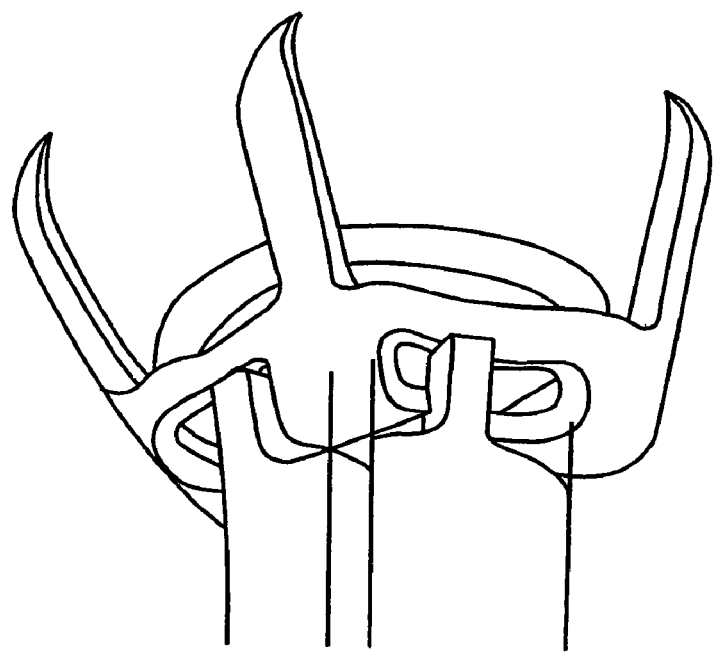
Figure 10A:
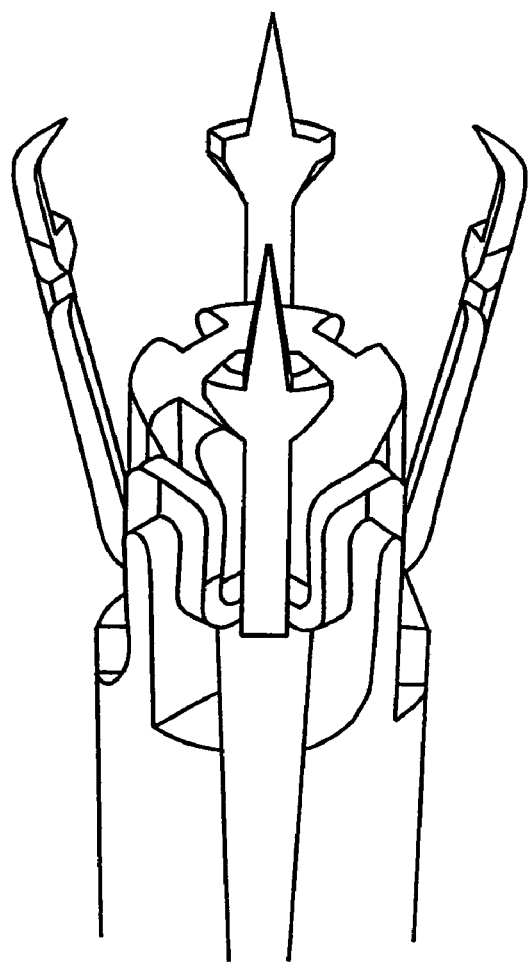
Figure 11B:
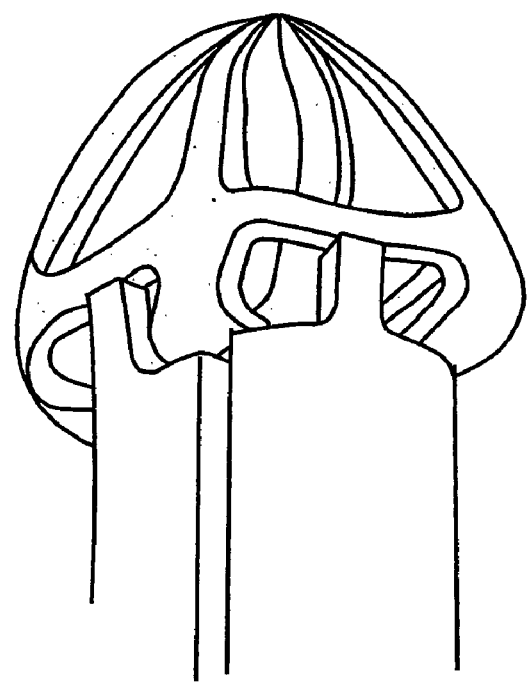
Figure 11A:
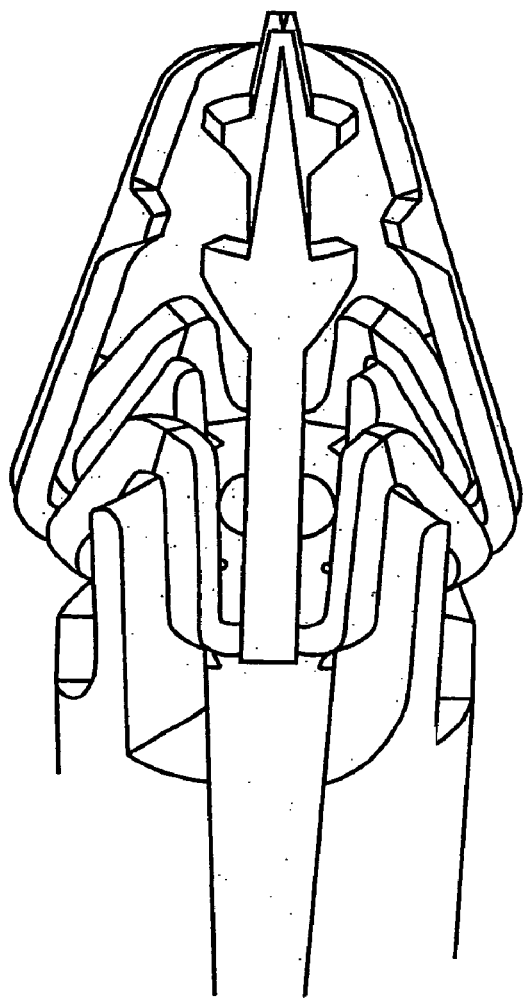

FIGS. 9, 10A, 10B, 11A and 11B depict the working relationship between the staple 10' and/or 50 of the present invention and the mandrel 114/sleeve 112 of the stapler mechanism 200. In FIG. 9A, the staple 10' is placed between the mandrel 114 and sleeve 112. Slots 20A-20D of the staple engage fingers 116A-116D of the sleeve. The prongs 12A-12D of the staple are dimensioned so as to fit over the mandrel, and tabs 14A-14D are dimensioned so as to fit over the rod 110, as shown. Similarly, for the staple 50 shown in FIG. 9B the staple 50 engages the mandrel 114 and sleeve 112 (not shown). This is a static position, as no forces are applied to the staple to cause deformation. In FIG. 10A, the staple 10' is urged into the first deformed position (of FIG. 2) by the relative movement of the rod/mandrel and the sleeve. As shown, the mandrel is urged proximally. As the mandrel moves, the tabs of the staple meet the narrowest part of the mandrel. Further movement forces the tabs to move outwardly, causing the prongs to likewise move outwardly (as described above with reference to FIG. 2). Once the tabs clear the mandrel, outward movement of the tabs and prongs ceases. Similarly, in FIG. 10B, the movement of the mandrel forces webs to extend outwardly causing the prongs to extend outwardly (as described above with reference to FIG. 5). Once the webs clear the mandrel, outward movement of the prongs ceases. FIG. 11A depicts final deployment of the staple into tissue. As the mandrel is drawn further proximally and once the tabs have cleared the mandrel, the shoulders (not shown) are spread outward, forcing the prongs to move together (toward the centerline axis) and closing tissue therebetween. FIG. 11B depicts the same actuation, but for the staple 50 of FIGS. 4-6.

Figure 12:
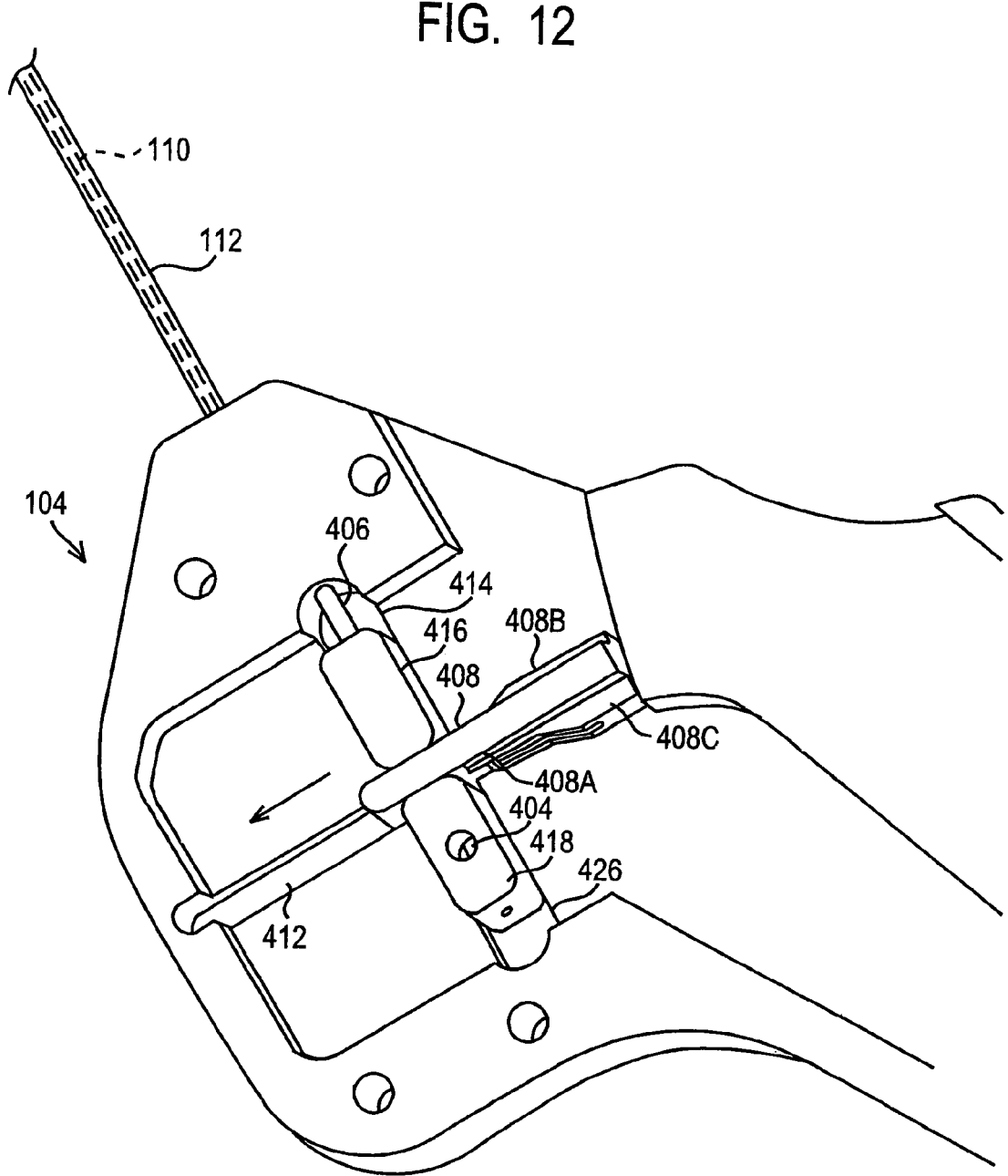
FIGS. 12-15 are isometric views of an exemplary staple deployment mechanism of the stapler of the present invention.

FIGS. 12-15 depict an exemplary actuator mechanism 104, showing the relative motion of the sleeve 112 and the mandrel rod 110. The mechanism includes a cam 408 movable in a linear motion along a slot 412. Movement of the cam can be manual or through an electronically controllable motor (not shown). The cam 408 has lobes 408A and 408C located on a first side of the cam 408 and a lobe 408B located on a second and opposing side of the cam 408. A first cam follower 418 is coupled to the mandrel rod 110, and is selectably engagable with lobes 408A and 408C. A second cam follower 416 is coupled to the sleeve 112, and is selectably engagable with lobe 408B. FIG. 12 depicts that neither cam follower is in contact with the lobes, and is indicative of an initial position of the mechanism.

Figure 13:
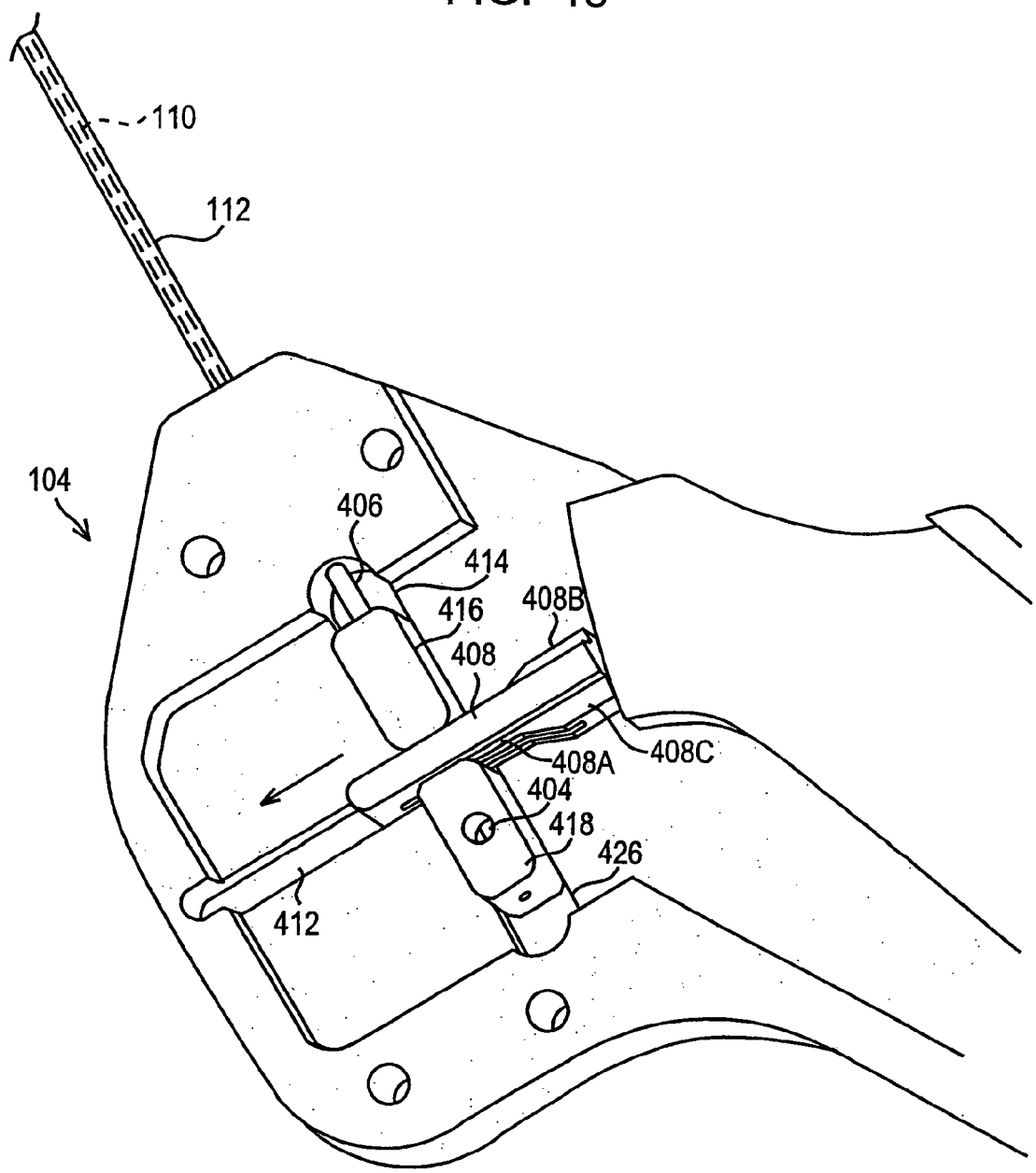
Figure 14:
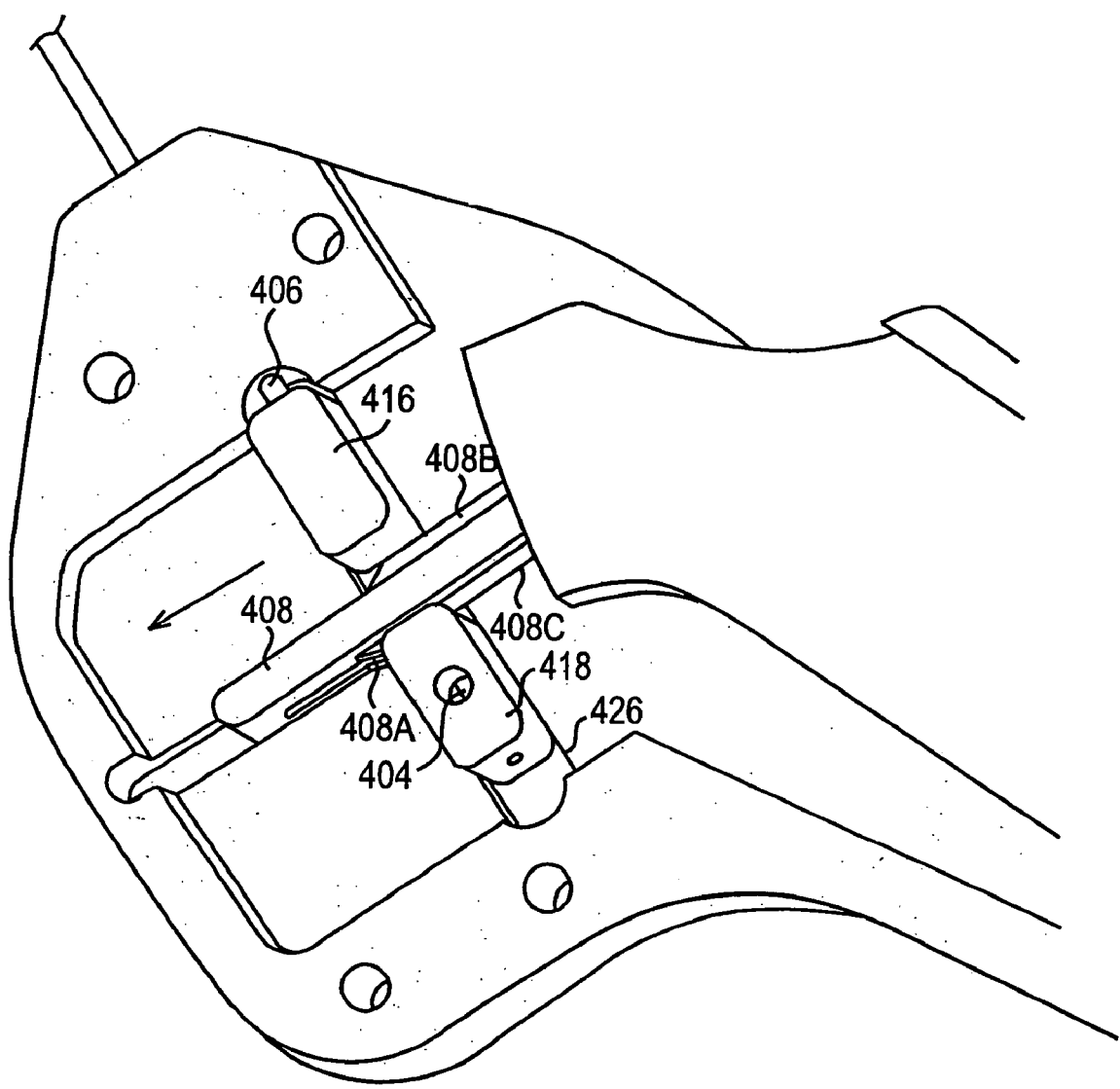
Figure 15:
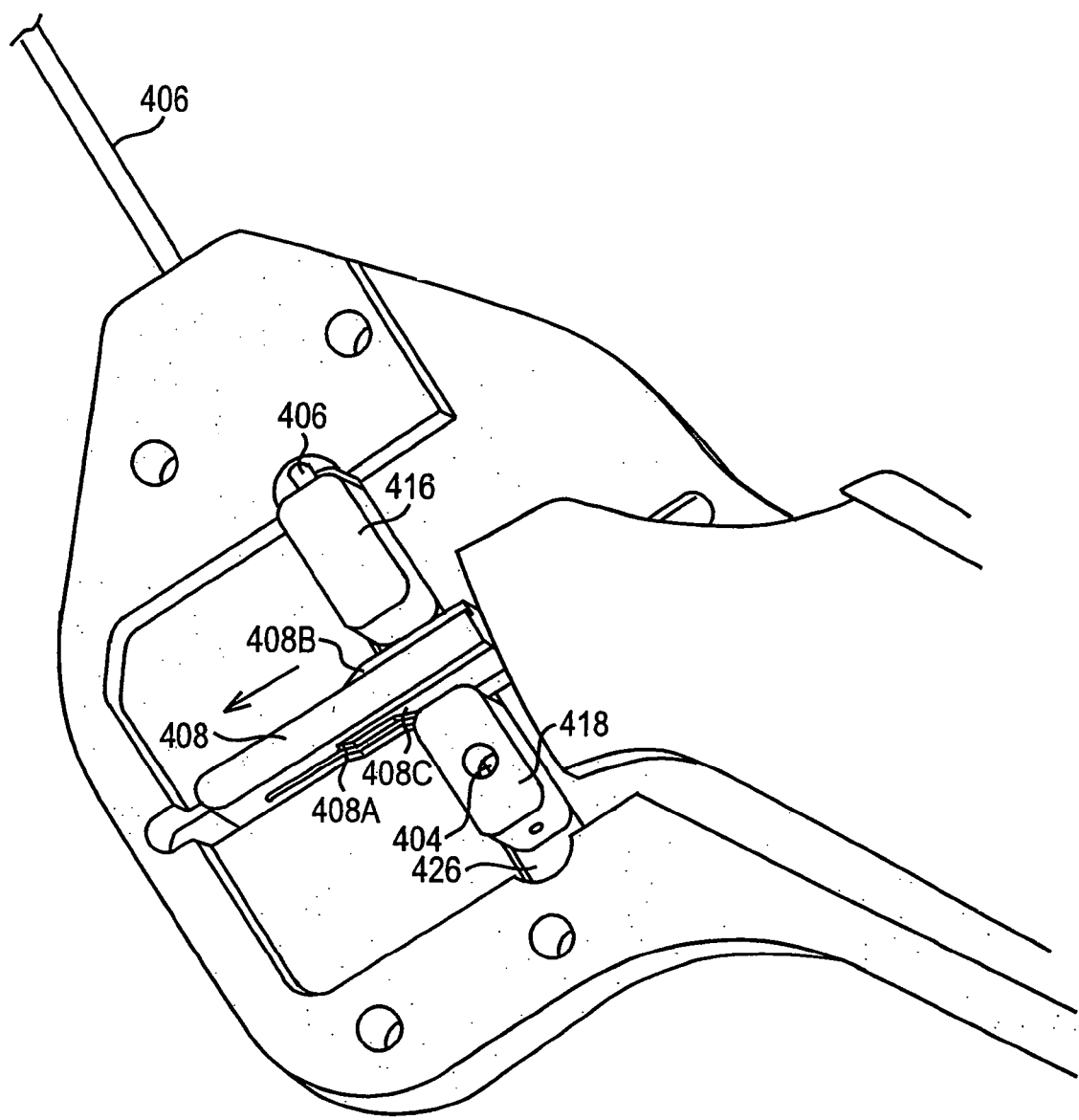

FIG. 13 depicts the mechanism 104 in a position to expand the staple between the mandrel 114 and the sleeve 112, as shown in FIG. 9A. As cam 408 is moved (as indicated by the arrow), lobe 408A urges cam follower 418 along slot 426. The mandrel rod 110 is moved proximally, causing the prongs to extend outwardly (as shown in FIGS. 2 and 5) as a result of the force of the mandrel 114 on the tabs or the web portions. With further movement of the cam 408 (FIG. 14), lobe 408B now urges cam follower 416 to move distally, thereby moving the sleeve distally relative to the mandrel rod and causing further expansion of the prongs and causing the staple to move distally. Finally, in FIG. 15, the cam is urged yet further and cam follower 418 is urged by lobe 408C causing the mandrel and madrel rod to extend further proximally. This relative movement between the cam rod and the sleeve causes the mandrel to apply a force to the shoulder portions of the staple, in turn causing inward movement of the prongs. Lobe 408C causes closure of the prongs and decouples the staple from the mandrel. This is the fully deployed staple movement.

Figure 16:
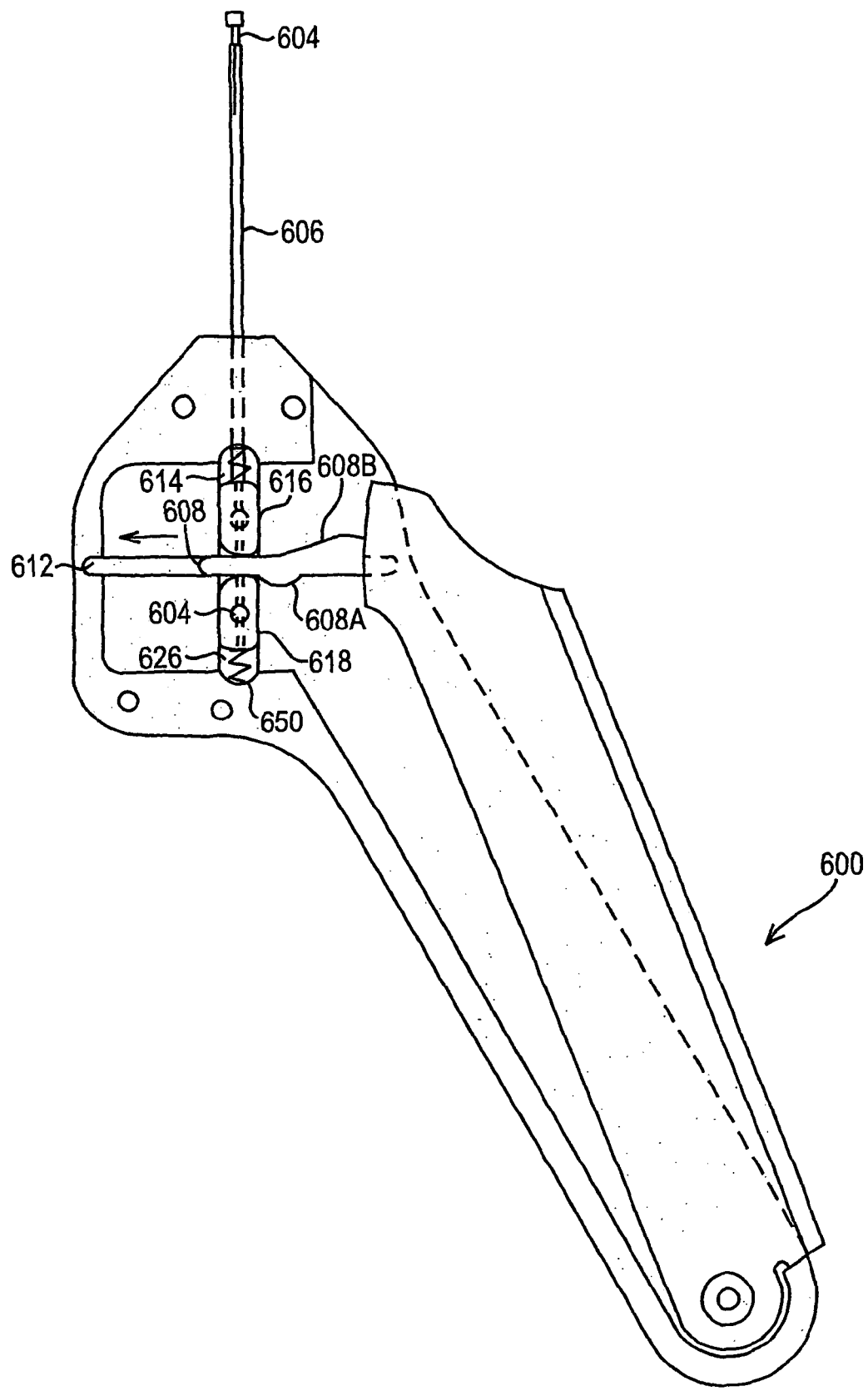
FIGS. 16 and 17 are isometric views of another exemplary staple deployment mechanism of the stapler of the present invention.
Figure 17:
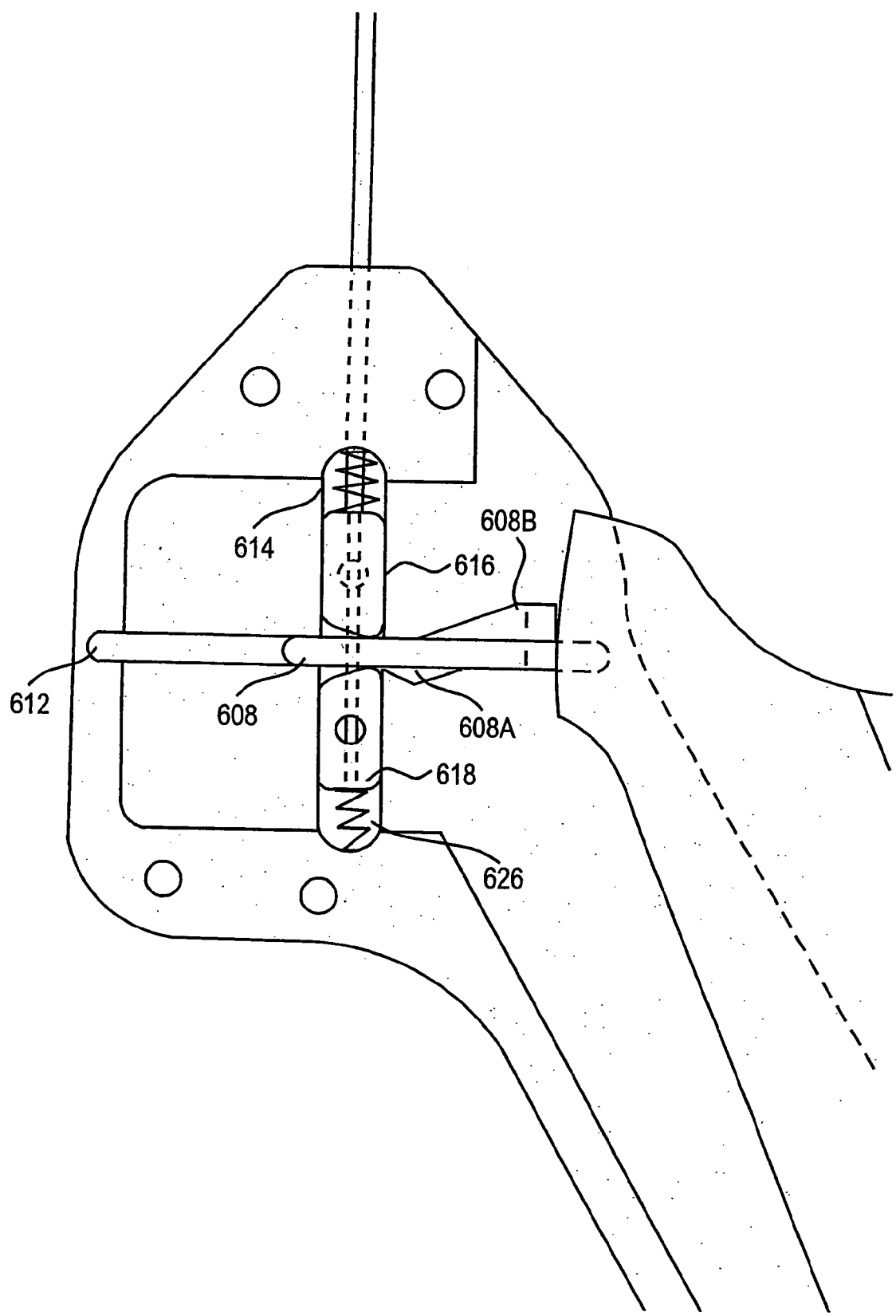

FIGS. 16 and 17 show an alternative cam mechanism. Similar to the previous example, cam 608 is urged in a direction indicated by the arrow to cause relative motion between the mandrel rod and the sleeve. Lobes 608A and 608B are located on opposite sides of cam 608. As the cam 608 is moved along slot 612, the lobe 608A urges a cam follower 618 in a linear motion along a slot 626. This urges the cam follower 618 proximally. The cam follower 618 is coupled to a mandrel rod 604. This deforms staple 10/50 in the second configuration (see FIG. 2 or 5). As the cam 608 is urged further, the cam follower 618 moves distally to stay in contact with the lobe 608A. This urges mandrel rod 604 distally. The same movement of the cam 608 urges lobe 608B to urge cam follower 616 distally. The cam follower 616 is coupled to a sleeve 606. This urges sleeve 606 distally. The downward slope of lobe 608A is parallel with upward slope of lobe 608B so the mandrel rod 604 and the sleeve 606 move distally in unison and the staple is advanced into the tissue. The movement of the cam follower 618 down the slope of lobe 608A then ceases while the movement of cam follower 616 continues up the slope of lobe 608B, the staple 10/50 is deformed into the closed or deployed configuration (see FIG. 3 or 6). Springs 614 and 650 can be provided to return cam followers 616 and 618, respectively, to an initial position. Of course an additional spring can be provided in slot 612 to move cam 608 back to an original position.

Alternatively, the actuation mechanism can include a rotating drum (not shown) to replace the cam 408 and 612. The drum may be adapted with lobes formed thereon, similar to lobes 408A-408C and 608A-608B, respectively. Other alternatives may include a rotating screw having a variable width in accordance with lobes 408A-408C or 608A-608B to actuate the mandrel rod and/or sleeve. Of course, instead of the cam mechanisms depicted in the Figures, direct linkage may be used to actuate the mandrel rod and/or sleeve.

Wound Site Management

Figure 18:
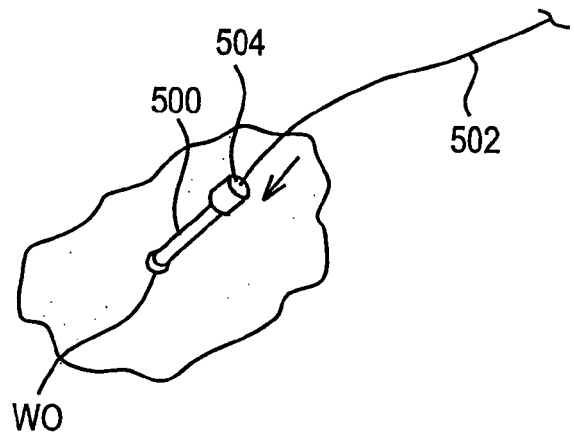
Figure 19:
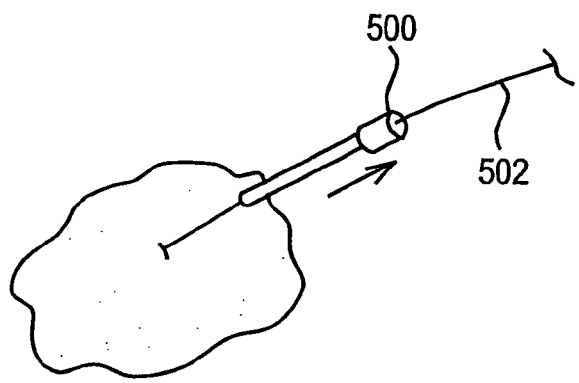

FIGS. 18-25A depict structural and procedural embodiments of wound site management during and after a medical procedure, such as angioplasty. FIG. 18 depicts a conventional tubular dilator 500 extending through the skin of a patient. Typically, the dilator 500 is left in the skin following a completed medical procedure. When the medical procedure has been completed, the wound site must be stabilized. Although the blood flow may not be completely stopped, the blood flow is reduced to a point where the coagulants in the blood can complete the wound closure. To start the stabilization process of the wound site, the doctor inserts a flexible guide wire 502 through an opening 504 in the end of the dilator 500. FIG. 19 shows the step of removing the introducer 500 from the wound site after the guide wire 502 is properly inserted through the skin and into the artery.

Figure 20:
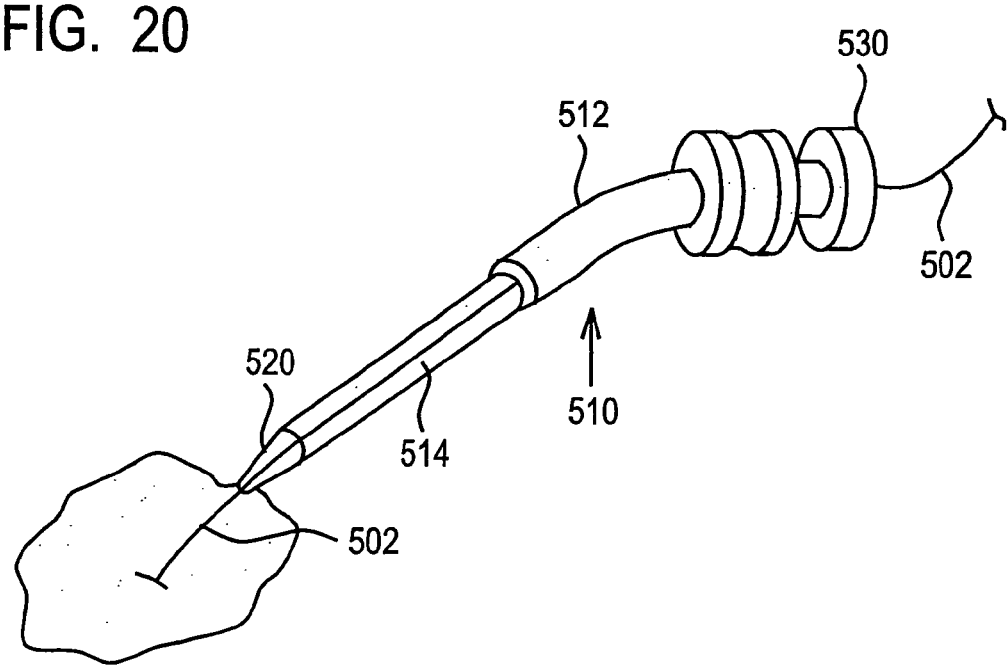

To facilitate efficient wound closure, another aspect of the present invention provides an introducer formed to stretch the wound site for more efficient and effective closure. FIG. 20 depicts an exemplary introducer 510 of the present invention, and continues the process from FIGS. 18 and 19 where the introducer 510 slides over the guide wire 502 through an opening in the introducer 510 and a portion of the introducer is placed into the artery. Details of the introducer 510 are disclosed below.

Figure 20A:
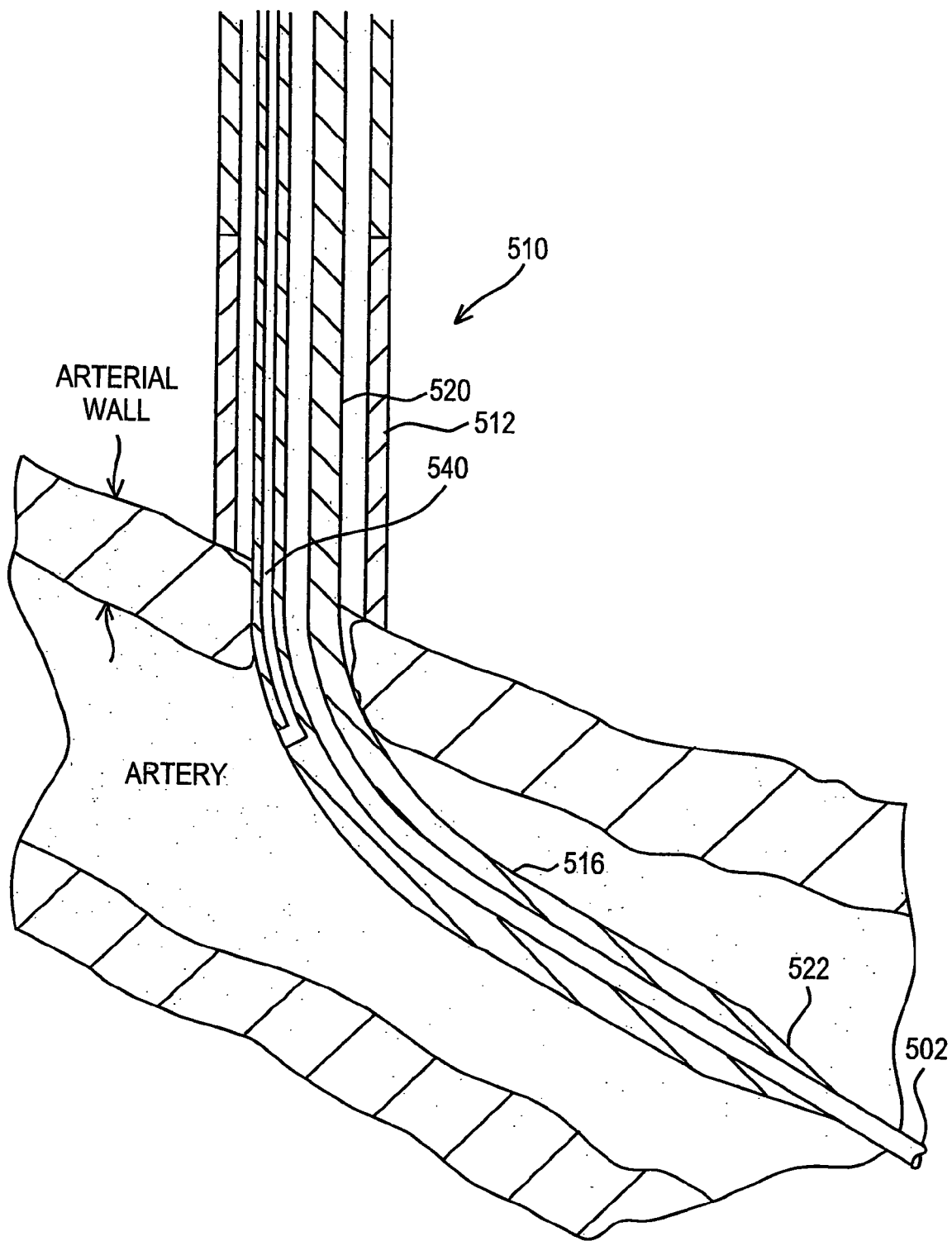

FIG. 20 depicts the introducer 510 inserted over the guide wire 502 (already in the artery) and inserted into the artery. The introducer includes a hollow elongated guide sheath 512 and dilator 520. Referring to FIG. 20A, the doctor urges the distal tip 516 of the dilator 520 into and through the guide sheath 512 (over guide wire 502). A flexible distal end 516 of the dilator 520 is inserted into the wound, until a blood marker BM indicates that the dilator 520 is properly positioned in the artery. The blood marker BM located at a predetermined length along the dilator 520 allows blood to flow through a cavity 540 to alert the doctor that the dilator 520, and more specifically the flexible distal tip 516, is properly inserted in an artery. Most preferable, the distal tip 516 of the dilator includes a tapered portion 522 to facilitate easier ingress into the artery. An additional blood marking passageway (not shown) can be included on the distal end of sheath 512 as precautionary indicator of the depth of the sheath. Presence of blood in this additional passageway is indicative of the sheath being pressed too far and into the arterial wall or into the artery. Of course, those skilled in the art will recognize that the introducer 510 will include internal passageways (lumens) for blood marking and the guide wire.

The diameter of distal end of the guide sheath 512 may be formed to expand if outward pressure is applied from inside surface of the guide sheath 512. For example, slits or weakened tear seams (described below) may be formed in the distal end of the guide sheath 512 to allow the diameter of the guide sheath to increase when pressure is applied.

Figure 21:
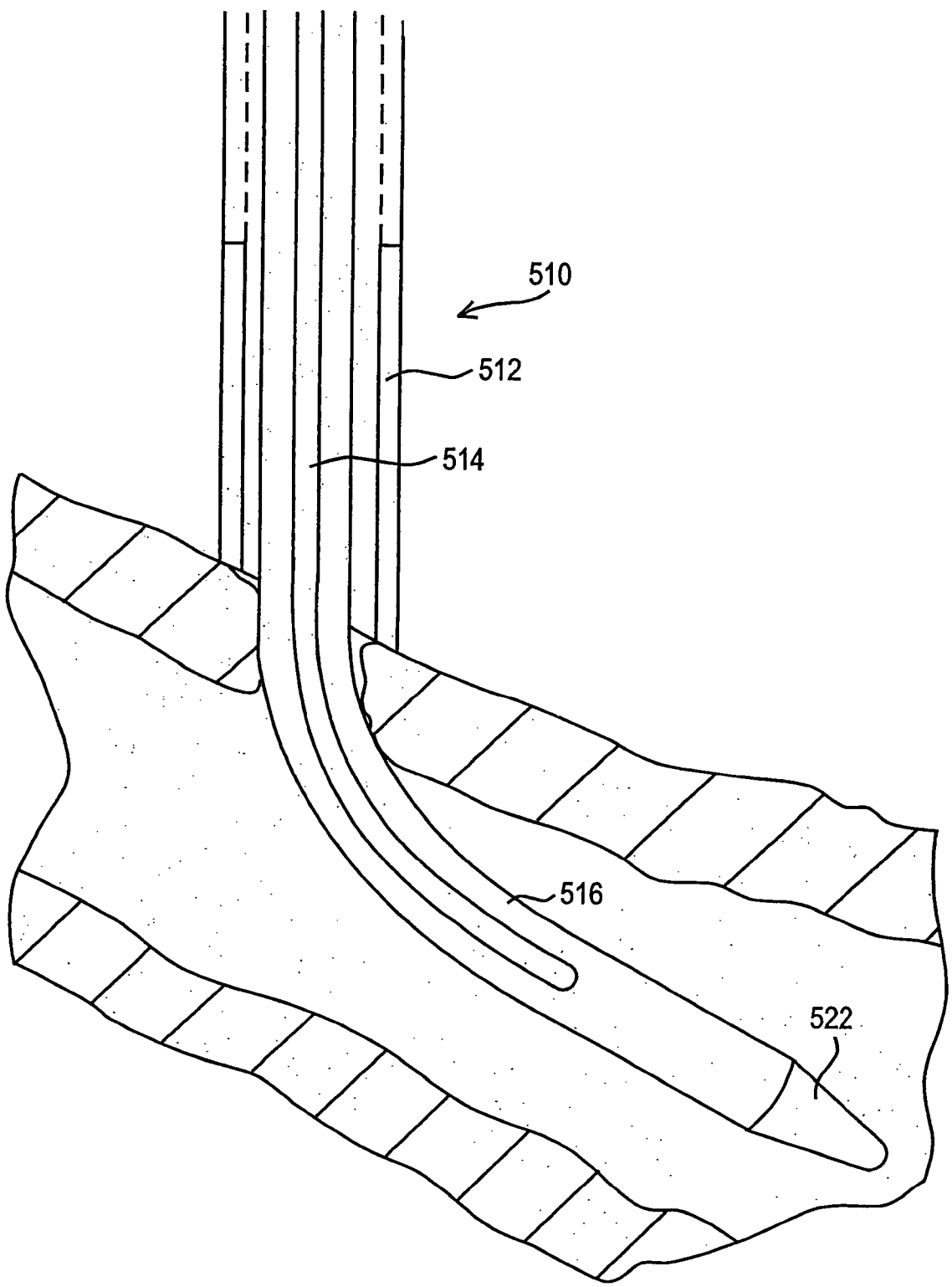
Figure 26:
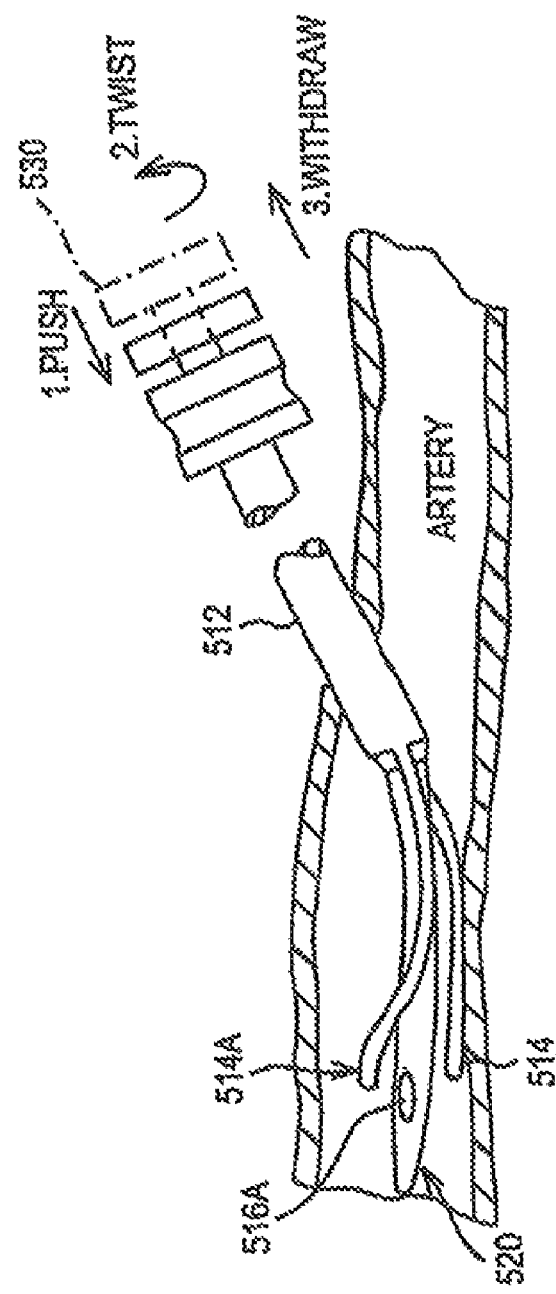

One feature of the guide sheath of this exemplary embodiment is the use of two or more wire guides 514 to maintain the sheath located on the wound site, to provide approximation of opposing sides of the wound, to ensure that the closure device (e.g., stapler/staple, suturing device, cauterization, etc) remains located about the wound so that a closure device is properly deployed, and to provide unobstructed access to the wound site. In this embodiment, wire guides 514 are formed on opposing sides of the guide sheath 512. Having the wire guides 514 on opposing sides helps to ensure that not only is the sheath located on the wound site, but that the sheath is approximately centered thereon. The wire guides are delivered into the artery by the dilator 520, as shown in FIGS. 21 and 26. The wire guides are removably coupled to the distal end 516 of the dilator 520 and deployed into the wound, as shown in FIG. 26. The wire guides can be releasably held in openings or slots (not shown) on the sides of dilator. Once the dilator is properly inserted into the wound to a proper depth (as indicated by the BM passageway), the dilator is removed from the wound and the guide sheath. To remove the dilator 520 from the guide sheath 512, the doctor (or clinician) first holds the guide sheath 512 and advances the dilator 520 inward (and upward) through the guide sheath 512. This decouples the guide wires 514A and 514B from the openings. To ensure that the wire guides 514A and 514B properly decouple from the dilator 520 before the dilator is withdrawn, a mechanism is provided that does not allow withdrawal until the guide rod has been inserted a predetermined distance. As shown in the drawing this mechanism can include a hub mechanism that requires a twisting motion or other action prior to withdrawal. After the guide rod has been inserted the predetermined distance, the doctor extracts the guide rod. This leaves the guide sheath 512 centered on the wound with the wire guides 514A and 514B extending inside the wound.

Figure 23:
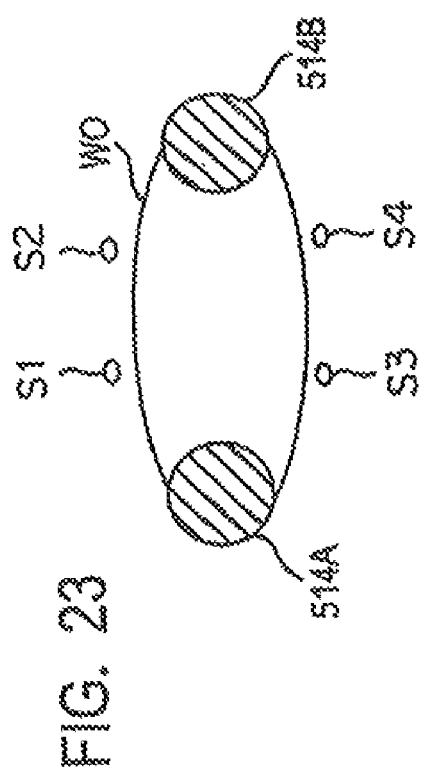

As is understood to those skilled in the diagnostic and interventional arts, a puncture in an artery or vein has a general tendency to manifest a slit or an elongated opening, since the cell structure forming this tissue forms circumferentially (rather than longitudinally) to support radial expansion and contraction of the vessel. The wire guides 514A and 514B of the present enable the wound to approximate the natural state of the wound, i.e., elongated circumferentially. The sheath may have a diameter approximately equal to the diameter of the opening or wound, so that the distance between the wire guides 514A and 514B on the sides of the sheath approximately equals the diameter of the long axis of the wound, as best shown in FIG. 23. Once inside the vessel, the wire guides 514A and 514B in this position limit movement of the sheath along the long axis, and since the wound is elongated, movement along the short axis is likewise limited. In this embodiment, since the wire guides 514A and 514B are disposed on opposing sides of the sheath, any device inserted through the sheath will be approximately centered on the wound.

Importantly, since the wound opening tends to assume the shape shown in FIG. 23 even in the absence of the wire guides, the opposing tissue located along the short axis tends to approximate. The present invention takes advantage of this tendency. If the position of the wire guides define a diameter larger than the diameter of the wound, the tissue along the short axis tends to approximate more, because the tissue on the long axis is stretched, thereby creating tension on the wound site. In other words, in this configuration, the wire guides force the tissue on either side of the wound to come together. It will be appreciated by those skilled in this art that the amount of tension required will be tissue dependant, and thus, the overall diameter of the sheath and wire guides should be sized according to the wound size and tissue strength, and should not be sized to cause a tear in the tissue. For example, vascular tissue is relatively elastic, and can tolerate more tension than other tissues (e.g., dura-matter, duct tissue, bladder tissue, etc.). The sheath and dilator of the present invention take these factors into consideration and are accordingly sized for the particular tissue application. However, sufficient wound site management according to the present invention does not require that the wire guides stretch the wound. Rather, if the position of the wire guides is shorter than the wound length, the wire guides still serve to maintain the sheath generally located (and possibly centered) on the wound. In both circumstances, the wire guides ensure that a closure (e.g., staple) deployment is more accurate. When tension is created on the wound site, a certain amount of tissue is available, which may be advantageously grasped by the staple for closure. Also, if the wound opening in the tissue is held taught by the sheath/wire guides, there is less tendency for the tissue surrounding the opening to slip down into the vessel during staple deployment (which would reduce the effectiveness of the closure).

FIG. 23 also shows examples of locations S1, S2, S3, and S4 of where the prongs of the staple to be inserted will line-up relative to the wound opening WO. The wire guides 514 are depicted disposed on opposing sides of the guide sheath 512, and more specifically, the wire guides are inserted into the wound opening along the long axis of the artery or vein, so that the wound is pulled taught along the long axis.

Figure 22:
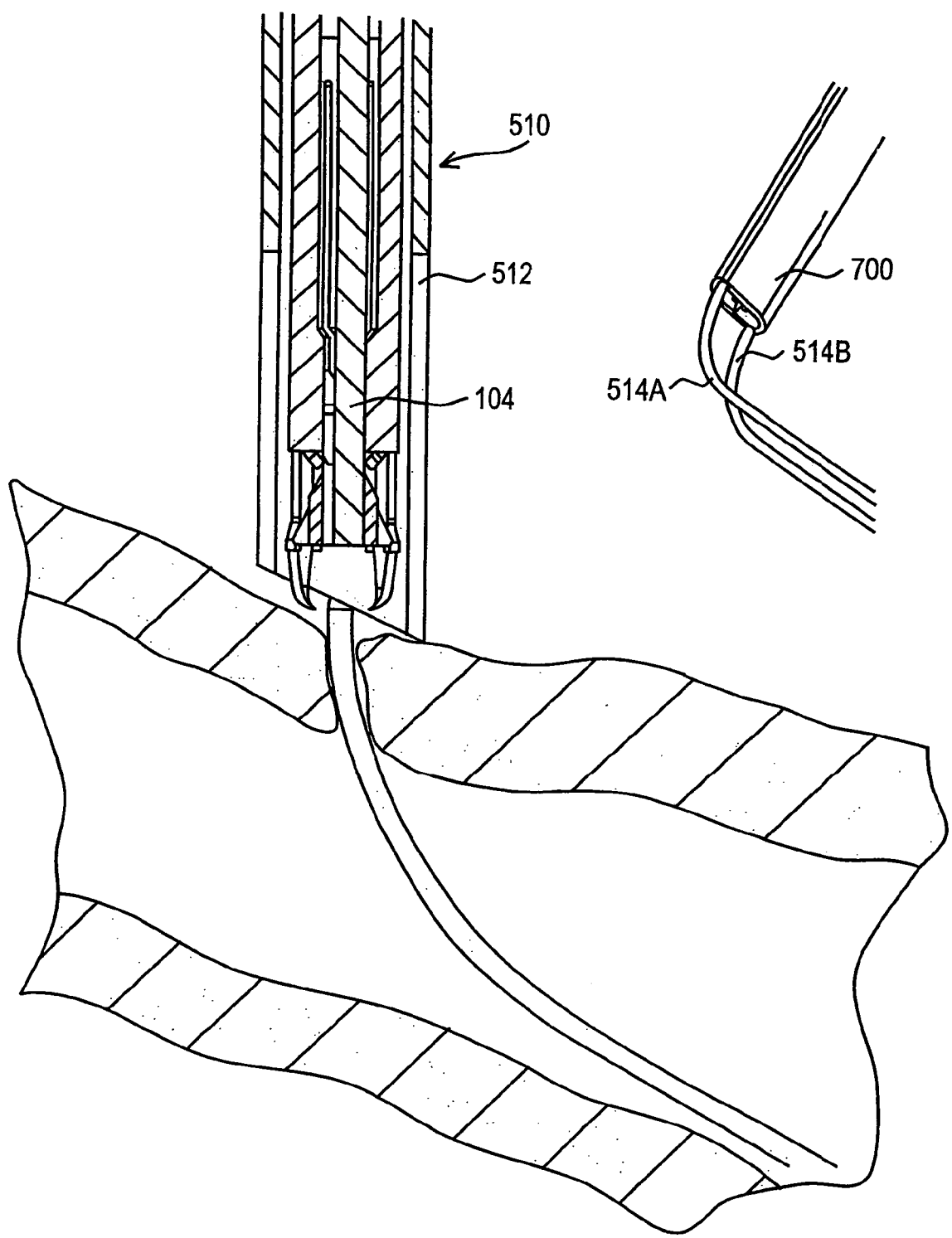
Figures 25, 25A:
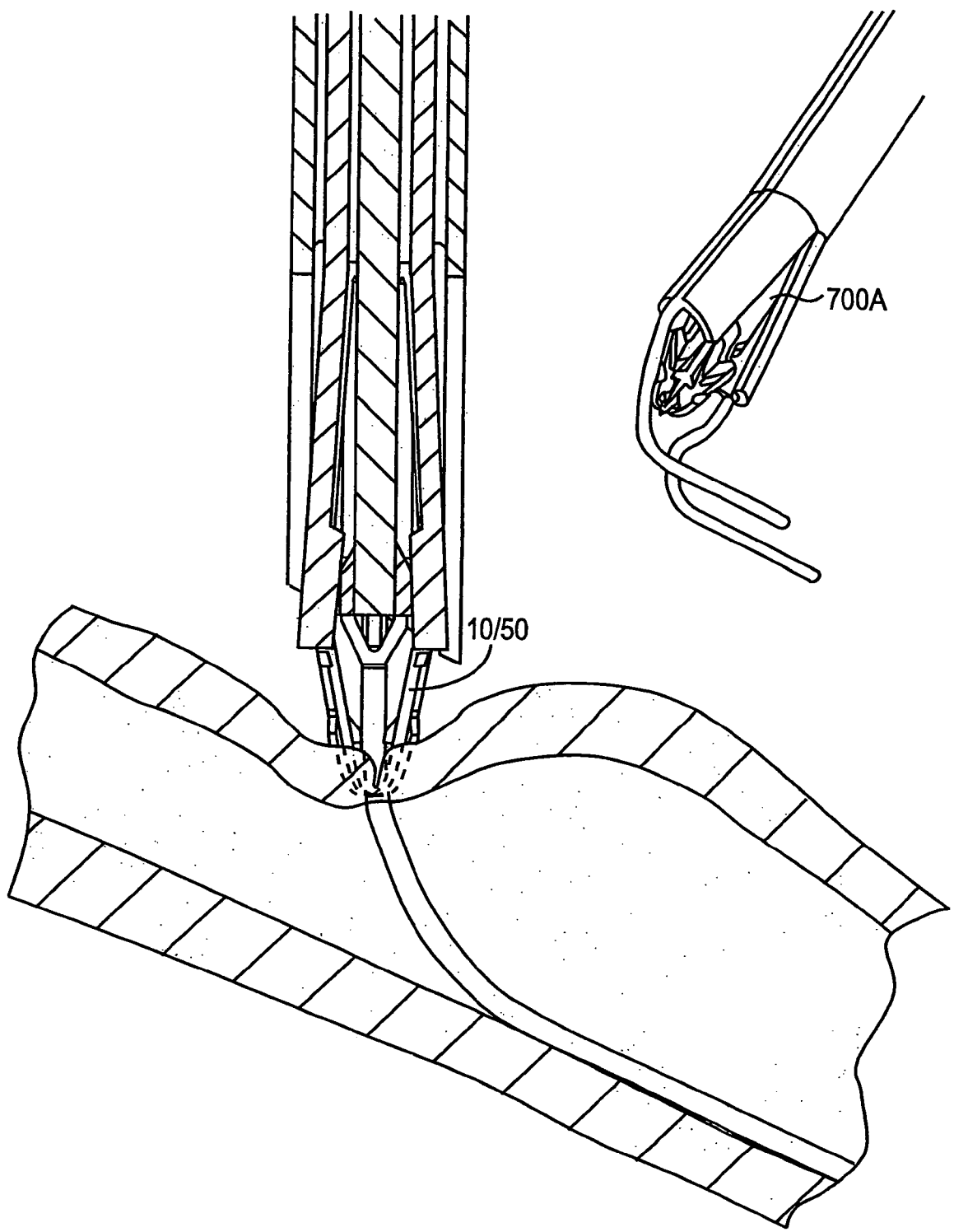

FIG. 22 shows the distal end of a stapler 104 with a staple 10/50 being inserted through the guide sheath 512 of the introducer 510. FIG. 22A depicts a relief view of the introducer 510, and more clearly depicts the slits or weakened tear seams 700. When the distal end of the stapler 104 is properly inserted in the guide sheath 512, the staple can be deployed into the tissue. FIG. 24 shows the first step of staple deployment, the process of which is described in detail above. Note that in FIG. 24A, the extension of the staple prongs causes the weakened tear seam or slits to separate. This further causes the wire guides to expand against the long axis of the wound, thereby further approximating the tissue surrounding the opening. The diameter formed by the prongs of the staple 10/50 is now larger than the original outside diameter of the guide sheath 512. FIGS. 25 and 25A depict the staple fully deployed into tissue, the process of which is described above. The stapler can now be removed from the guide sheath 512. The guide sheath 512 can now be urged away from the wound opening WO and the guide wires 514A and 514B are extracted from the closed opening.

In an alternative exemplary embodiment, instead of using wire guides, a single loop actuation wire 654 is used, as in the exemplary introducer assembly 510' illustrated in FIGS. 27-32. The exemplary introducer assembly 510' is slidably disposed about a central guide wire 672 and comprises a guide rod 670 and a guide sheath 662. The guide sheath 662 includes a plurality of wire stabilization guides 660, which may be integrated into the guide sheath 662, or alternatively, be formed separately and coupled thereto. The wire stabilization guides 660 generally comprise tubular members disposed around the outside diameter of the sheath, to hold the end portions 656, 657 of the loop actuation wire 654. Guide sheath 662 is a tubular and has a circular cross-sectional shape, and has an inside diameter dimensioned to slide over the guide rod 670. It is equally contemplated that the guide sheath has an oval or non-circular cross-sectional shape. The sheath further includes one or more slits or weakened tear seams 686 to provide controlled expansion of portions of the guide sheath, as will be detailed below.

Figure 27:
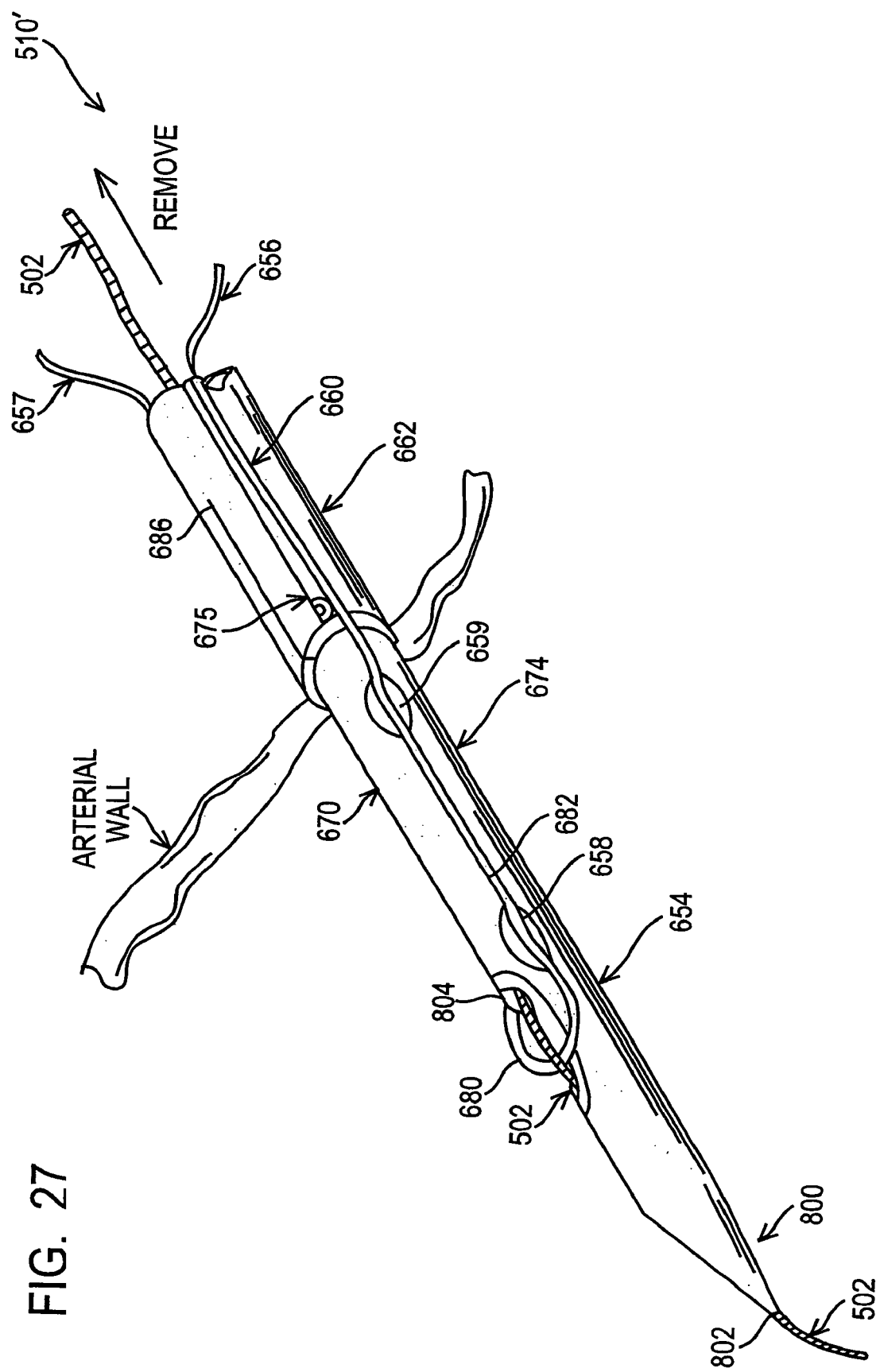

The guide rod 670 is a tubular member and includes at least one slot 682 formed therein for releasably holding the loop actuation wire 654. As shown in FIG. 27, the guide rod has a main tubular body dimensioned to fit inside the guide sheath and has a tapered end 800 having an opening 802 at the tip to accept the central guide wire. To releasably hold the actuation wire, at least one longitudinal slot 682 may be formed in the guide rod 670 along its length. To permit temporary holding and controlled release of the loop actuation wire 654, the width of the longitudinal slot 682 at the surface of the guide rod 670 should be less than the outside diameter of the stabilization guides 660 or the loop actuation wire 654, so that the stabilization guide and/or loop actuation wire 654 is held within the slot (as shown in FIG. 27) until released by the sliding action of the sheath over the guide rod, as described below. The loop actuation wire and/or wire guides can be held in a slot or slit formed in the guide rod (which may define a separate lumen structure in the guide rod), or alternatively the slot can be formed with a diameter less than the width of the wire or wire stabilization guide to permit the wire or wire stabilization guide to friction fit into the slot. As shown in FIGS. 27-29, the slot 682 may be bounded by a pair of recessed areas 658, 659, so that, for example, the wire does not catch on tissue as the guide rod is inserted and removed from an artery or vein. Alternatively, instead of defined slots formed in the guide rod, slits (not shown) may be formed in the material of the rod such that the loop actuation wire 654 is releasably held to the guide rod in a friction fit manner, and released from the guide rod in a similar manner as described above.

In this configuration, one end portion 656 of the loop actuation wire 654 is threaded inwardly into one end of the slot 682 at the first recessed area 658 and back outwardly from the slot 682 at the second recessed area 659 in the guide rod 670. Similarly, the other end portion 657 of the loop actuation wire 654 may be threaded through a second slot (not shown), which may optionally include a set of recessed areas (not shown) on the opposing side of the guide rod 670, or elsewhere along its length. The slot 682 may be located along the length of the guide rod 670. For example, as shown in FIGS. 27-32, the slot 682 is located along a line parallel to the central axis of the guide rod 670. Of course, it is not a requirement of the present invention that the slot be formed in this manner, nor that the slot include recessed areas at its ends. As used herein with reference to the location of the slot(s) 682 and/or recessed areas 658, 659, the phrase "along the length of the guide rod" or "along its length" may mean generally longitudinally along the central axis of the guide rod, or may alternatively mean a slot formed in any orientation, since the slot and/or recessed areas 658, 659 merely serve to releasably hold the wire stabilization guides 660 and/or ends 656, 657 of the loop activation wire in place, and one of any number of configurations of slot 682 and/or recessed areas 658, 659 may suffice. While not necessary to provide operability to the present invention, an opening 804 within the guide rod may be provide to expose a portion of the central guide wire 672. The central guide wire 672 can then be placed over the loop portion 680 of the loop actuation wire 654 to secure the loop to the guide rod until the central guide wire is removed. The foregoing assumed that the wire forming the wire actuation loop has a generally circular cross section. However, alternatively other wire shapes may be used, in which case the wire stabilization guides 660 and slot 682 may comprise one or more internal mating components adapted to mate with end portions 656, 657 of the loop actuation wire 654, in which case the end portions 656, 657 would comprise one or more appropriate corresponding mating components.

FIGS. 39 and 39A depict cross-sectional views of the guide rod 670 of this exemplary embodiment. The guide rod 670, as depicted in FIG. 40, includes a plurality of lumens: 802, 804, 806 and 808. Lumens 808 and 806 are included as a blood marking passageway (described above) and a wire guide passageway, respectively. Lumens 806 and 808 are shown adjacent one another, but these lumens could also be formed coaxial with on another (e.g., the wire guide lumen inside of the blood marking lumen). Lumens 802 and 804 releasably hold the loop actuation wire therein, and run along the length of the guide rod, for example, as shown in FIG. 27. Lumens 802 and 804 are shown on opposing sides of the guide rod. But it is equally contemplated that the lumens need not be disposed at opposition, but rather may be formed at any angle with respect to one another. A slit 810 may be provided such that the loop actuation wire is held in lumen 802/804 until outward pressure forces the wire to "pop" out of the slit 810. To that end, the material surrounding the slit may comprise material of reduced durometer (with respect to the rest of the guide rod) such that the actuation wire can slide into and out of the lumen. Alternatively, instead of a slit, a slot may be formed as depicted in FIG. 40A. The slot 812 is defined by truncated lobes 814 and 816. Lobes 814 and 816 may also comprise material of reduced durometer with respect to the remaining portions of the guide rod. Slot 812 can be dimensioned for a particular gage wire inserted therein. Although lumens 804 and 802 are depicted as having generally circular cross-sectional shapes, the present invention equally contemplates other shapes, as may be dictated by the cross-sectional shape of the loop actuation wire (although the cross sectional shape of the wire stabilization guide, loop actuation wire and the lumen need not match).

The use of the foregoing described exemplary introducer 510' will now proceed with reference to FIGS. 27-32. As FIG. 27 illustrates, the introducer 510' is initially inserted into the percutaneous puncture over the central guide wire 672 (already in the artery), which tracks into the puncture site, and is inserted into the artery. Once it has been determined that the distal end of the guide sheath 662 has reached the approximate location of the artery or venous outer wall, the central guide wire 672 may be removed from the introducer assembly 510', as shown. As shown in FIG. 28, removing the central guide wire 672 allows the loop activation wire 654 to be freely released from the guide rod 670 through the longitudinal apertures 682 within the guide rod 670. This is accomplished by withdrawing the guide rod 670 from the guide sheath 662 as shown in FIGS. 28 and 29. Removing the guide rod from the guide sheath forces the wire stabilization guides 660 (and the loop activation wire within) out of the slots 682 defined in the guide rod by virtue of the force of the end of the sheath on the wire stabilization guides as the guide rod slides proximally out of the sheath, whereupon the loop actuation wire 654 and wire stabilization guides 660 are released to form an open loop, as shown in FIG. 29. The guide rod 670 may then be completely withdrawn from the guide sheath 662.

Figure 30:
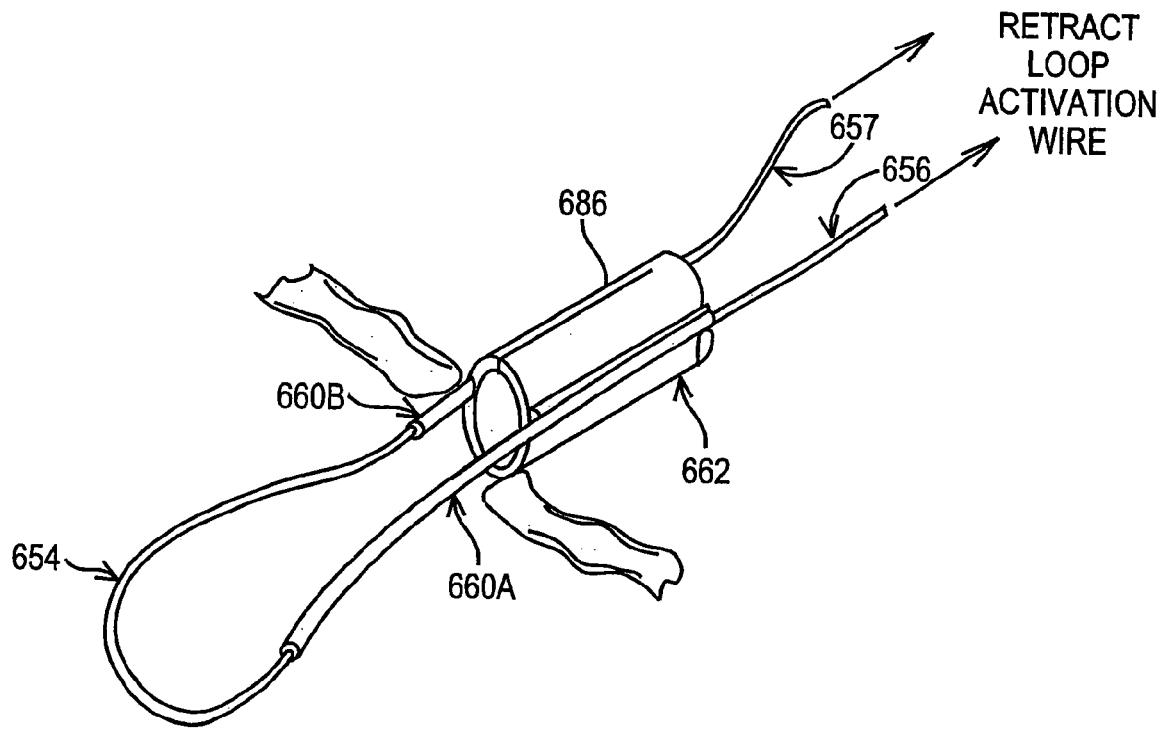
Figure 31:
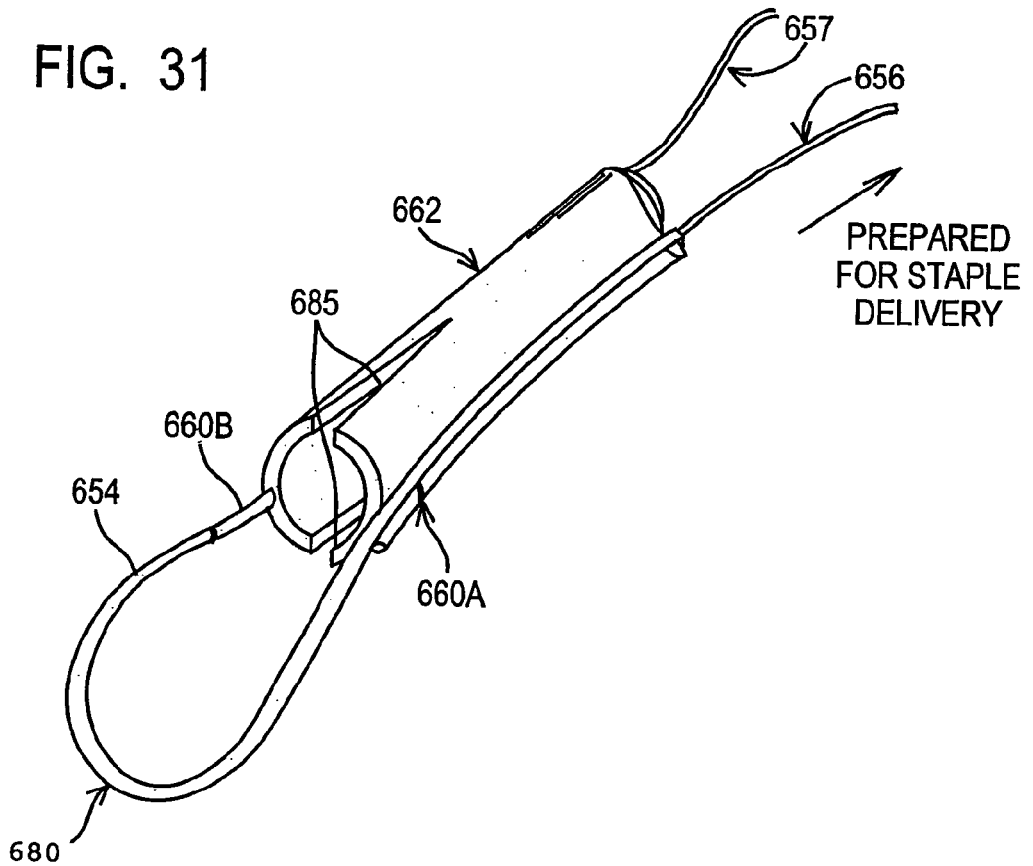
Figure 32:
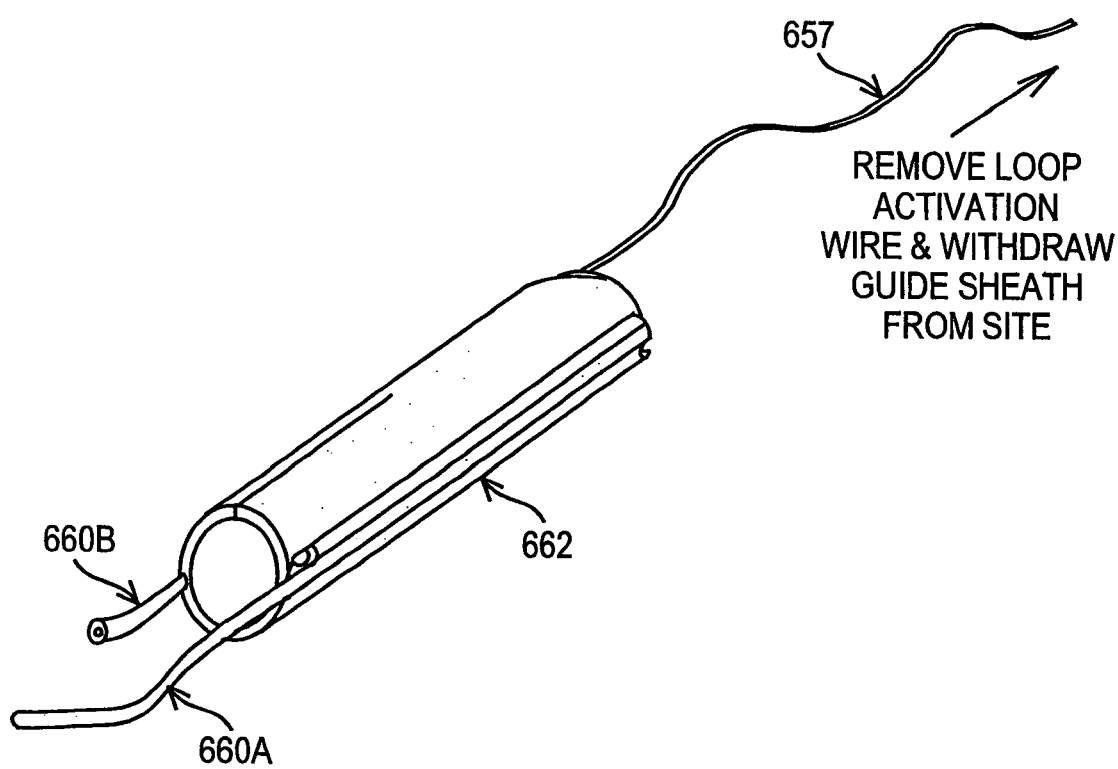

As FIGS. 30 and 31 illustrate, the stabilization guides 660 may be secured and actuated by pulling the loop actuation wire 654 at one or both end portions 656, 657 until the distal ends of the stabilization guides 660 approximate to form a stabilization loop portion 680. Preferably, slits 686 or weakened tear seams (slits and weakened tear seams are used synomously herein) are formed in the distal end of the guide sheath 662 to allow the diameter of the guide sheath 662 to increase when an outwardly radial force is applied to the distal end of the guide sheath 662, for example by the expansion of the loop portion of the loop actuation wire 654. The foregoing action provides opposing forces outwardly to the central axis of the guide sheath 662, thereby causing the end of the guide sheath 662 to separate at its slits 686. Additional clearance for the expansion of a closure device (not shown) within the guide sheath 662 is thus provided. Furthermore, the tissue that is stretched by the stabilization guides 660 is caused to slide along the newly ramped angles of the stabilization guides 660 and be forced against the distal end of the guide sheath 662. Moreover, the foregoing action aids in retaining the guide sheath 662 within the puncture against the vessel. The closure modality (e.g., a staple, as described hereinabove) may next be delivered. As shown in FIG. 32, tension may then be applied to a single end 657 of the loop actuation wire 654 until the wire 654 is completely removed from the plurality of stabilization guides 660, thereby freeing the distal ends of the stabilization guides 660 and allowing them to slide out of the vessel puncture on either side of the closure device (not shown). Finally, the guide sheath 662 assembly may be removed from the puncture site.

The wire stabilization guides 660A and 660B depicted in FIGS. 30-32 are generally formed as tubular structures having an inside diameter sufficient to pass the wire ends 656, 657 therethrough. The guide 660A and 660B are drawn together (FIG. 31) to form the loop. As a general matter, the wire stabilization guides 660A and 660B in combination with the loop activation wire add to the stiffness of the combined area, since it is intended that the closure of the guides causes sufficient outward force to expand the sheath along the slot or weakened tear seams, i.e. by creating a loop causing these outward forces. Note that the Figures depict wire guide 660A longer than 660B, however, it is not essential that the lengths of the wire guides are as depicted. Rather, the lengths may be selected to be equal or non-equal without departing from the present invention. The positions of the wire guides 660A and 660B are depicted on opposing sides of the sheath. While this arrangement will provide a more accurate centering of the sheath on the wound site, it is contemplated herein that for certain procedures centering on the wound site may not be necessary, critical, or accurate, and thus, the positions of the wire stabilization guides can be at locations about the sheath other than at opposition.

Note also that the description of the slots in the guide rod to releasably hold the wire stabilization guides are formed in a location most convenient for placing the wire guides into the slots. Also, the slots may be defined such that one slot releasably holds the wire stabilization guide with the wire inserted therethrough, and the other slot is dimensioned to releasably hold just the wire (as may be the case when the lengths of the wire stabilization guides differ). Still other modification may be made.

Thus, a single or multi-lumen sheath device may be stabilized in direct approximation to an arterial, venous or other lumenal puncture. Advantageously, the foregoing described method allows the positioning of a closure modality directly centered over such a puncture. The foregoing described introducer assembly 510' allows the distal end of the sheath 662 through which the closure device is introduced to be drawn against the artery, vein or other lumen, thereby aiding in sealing the puncture site to prevent leakage, as well as stabilizing the sheath 662 directly over the wound site.

Figure 35:
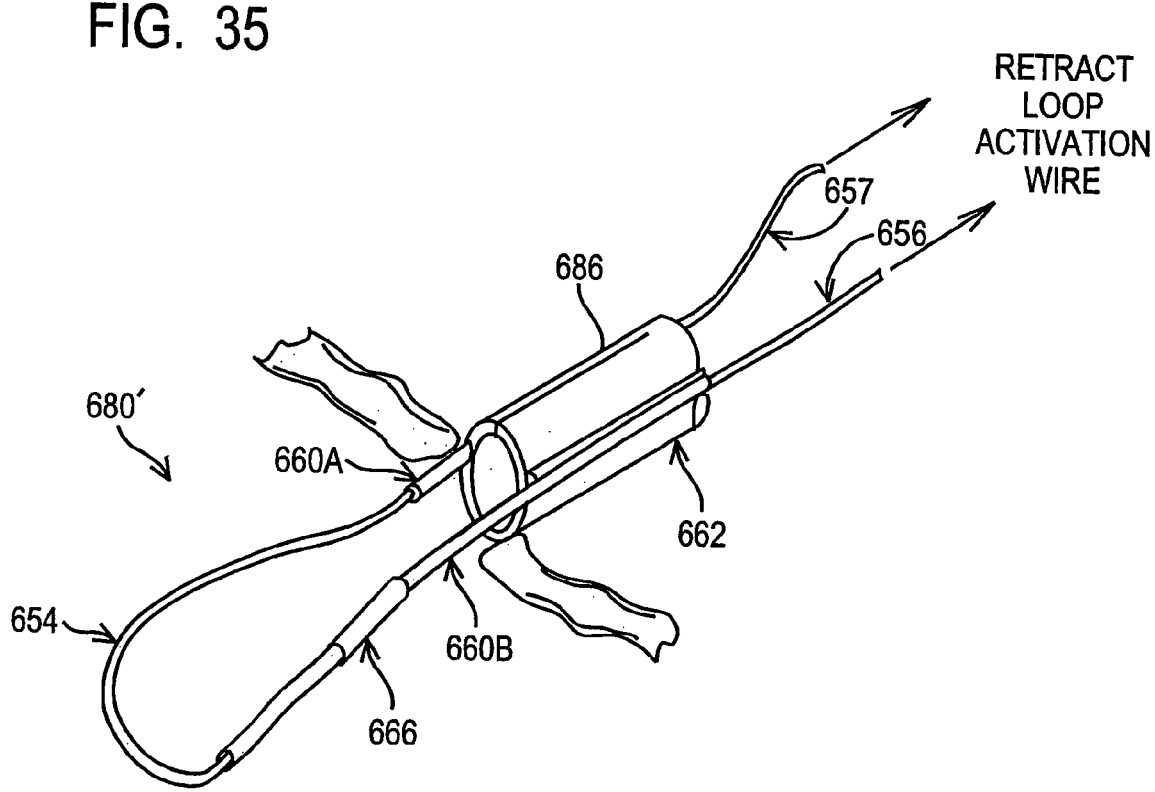
FIGS. 35 and 36 are isometric views of another exemplary embodiment of an introducer of the present invention.
Figure 36:
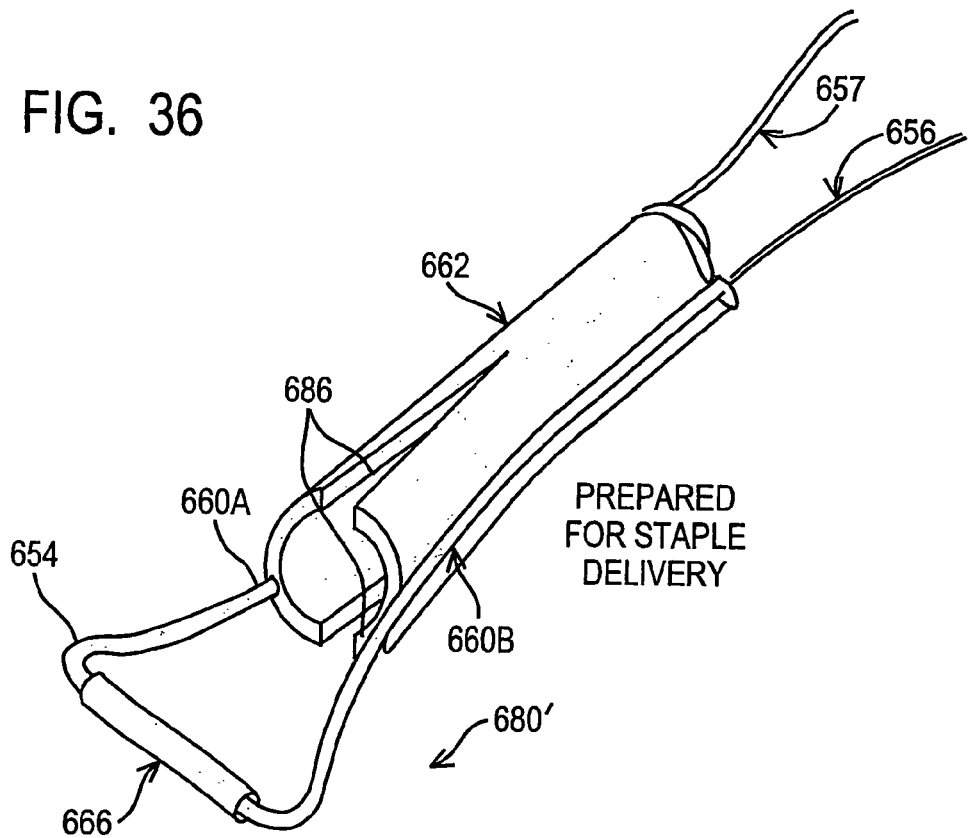

As FIGS. 35 and 36 illustrate, in another embodiment, the foregoing described stabilization loop portion may be replaced with a stabilization loop portion 680' comprising a loop actuation wire 654 having at least one reinforced section 666. The reinforced section may comprise an area of increased material or combination of materials, e.g., a section of the actuation wire 654 or stabilization guide 660 with greater individual or combined rigidity. In this configuration, the location of the reinforced section 666 may be manipulated with respect to the wound site to control the shape of the stabilization loop portion 680'. The stabilization guides 660 may be secured and actuated by pulling the loop actuation wire 654 at one or both end portions 656, 657 until the distal ends of the stabilization guides 660 approximate to form a stabilization loop portion 680' which comprises the reinforced section 666, the central axis of which is generally perpendicular to the central axis of the guide sheath 662, thereby providing opposing forces outwardly perpendicular to the central axis of the guide sheath 662 and causing the end of the guide sheath 662 to separate at its slits 686. As shown in FIG. 36, the loop portion and reinforced section forms a shape with the general appearance of coat hanger. Additional clearance for the expansion of a closure device (not shown) within the guide sheath 662 may likewise be provided.

Figure 33:
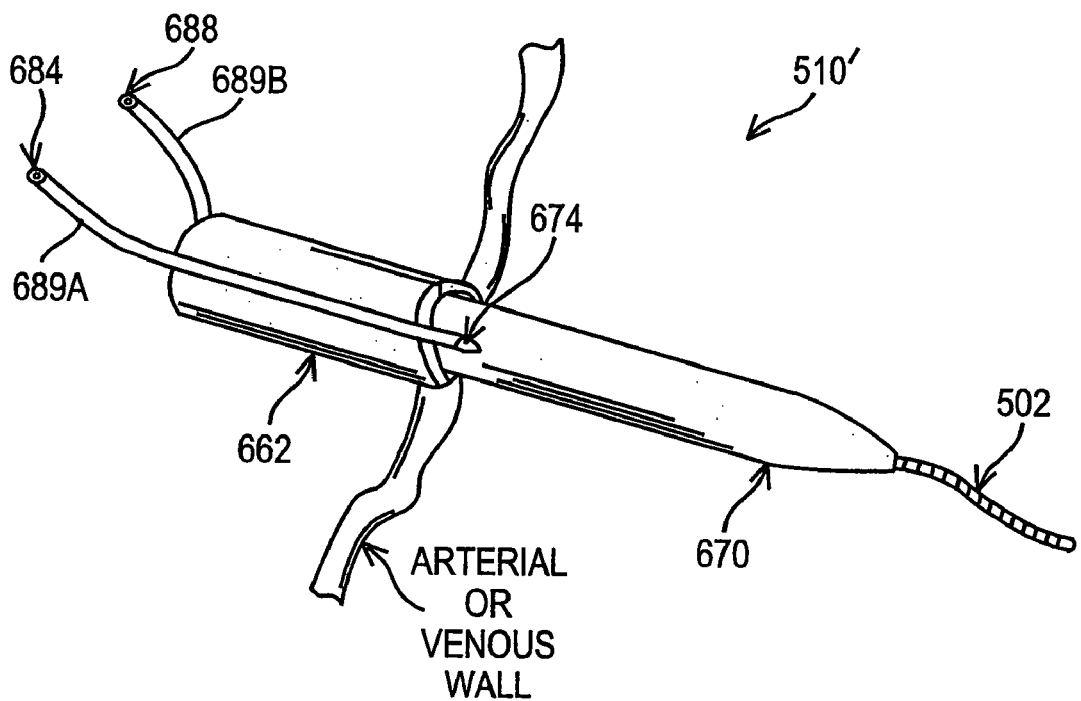
Figure 34:
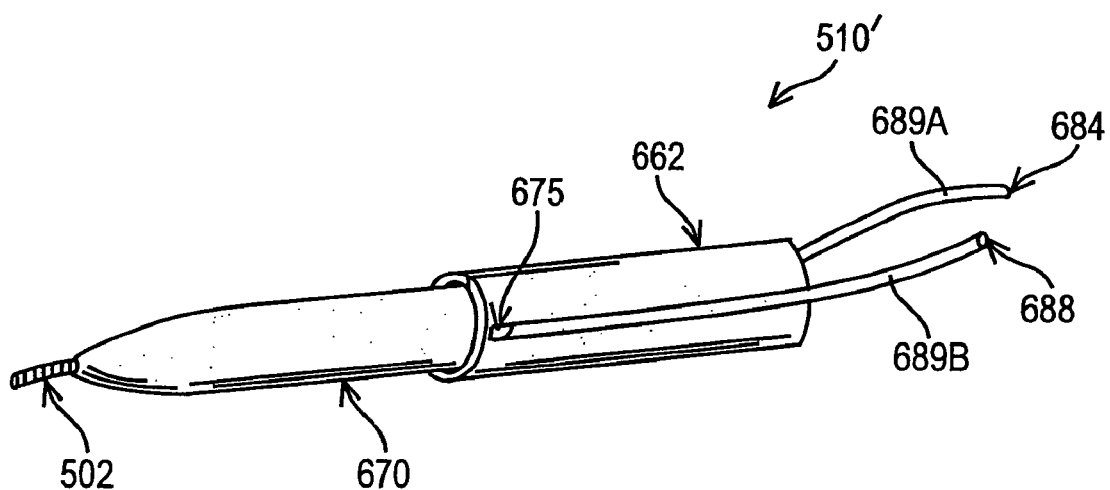

As in the previously described embodiment, the tissue which is stretched by the stabilization guides 660 is caused to slide along the newly ramped angles of the stabilization guides 660 and be forced against the distal end of the guide sheath 662. The foregoing action aids in retaining the guide sheath 662 within the puncture against the vessel. The closure modality (e.g., a staple, as described hereinabove) may next be delivered. As shown in FIG. 32, tension may then be applied to a single end 657 of the loop actuation wire 654 until the wire 654 is completely removed from the plurality of stabilization guides 660, thereby freeing the distal ends of the stabilization guides 660 and allowing them to slide out of the vessel puncture on either side of the closure device (not shown). Finally, the guide sheath 662 assembly may be removed from the puncture site. As those skilled in the art will recognize, in the foregoing described procedure illustrated in FIGS. 27-32, it is necessary for the doctor to determine the point at which the distal end of the guide sheath 662 has reached the approximate location of the artery or venous outer wall prior to removing the central guide wire 672 from the introducer assembly 510'. One exemplary method for identifying insertion depth of a transluminal device will now be described with reference to FIGS. 33 and 34. As shown, two "flash back" blood marking lumens 689 are fixedly attached to the guide sheath 662. The distal end of the first blood marking lumen is at an interluminal blood marking port 674 located at a predetermined point along the guide rod 670, and the proximal end of the first blood marking lumen is an interluminal flashback port 684 for observing the presence of blood at the interluminal blood marking port 674. The distal end of the second blood marking lumen is an extraluminal blood marking port 675 located approximately at the distal end of the guide sheath 662, and the proximal end of the second blood marking lumen is an extraluminal flashback port 688 for observing the presence of blood at the extraluminal blood marking port 675.

In operation, the introducer assembly 510' is introduced into the percutaneous puncture which tracks into the puncture site, as described hereinabove. The location at which the guide sheath 662 has reached the approximate location of the artery or venous outer wall may be identified by observing the pressurized blood flow from the internal flashback port 684, which enters the internal blood marking port 674 when the internal blood marking port 674 has reached the inner lumen of the vessel. The absence of pressurized blood flow observed at the internal flashback port 684 indicates that the guide sheath 662 has not yet reached the vessel outer wall. The fact that the guide sheath 662 has not entered the inner lumen of the vessel may be confirmed by the absence of pressurized blood flow observed at the external flashback port 688, which enters the extraluminal blood marking port 675 only if the extraluminal blood marking port 675 has reached the inner lumen of the vessel. Likewise, presence of blood in this lumen indicates the guide is too far into the artery or vein. The presence of pressurized blood flow at the internal flashback port 684 and absence of pressurized blood flow at the external flashback port 688 indicate that the distal end of the guide sheath 662 is adjacent to the arterial or venous outer wall.

Figure 37:
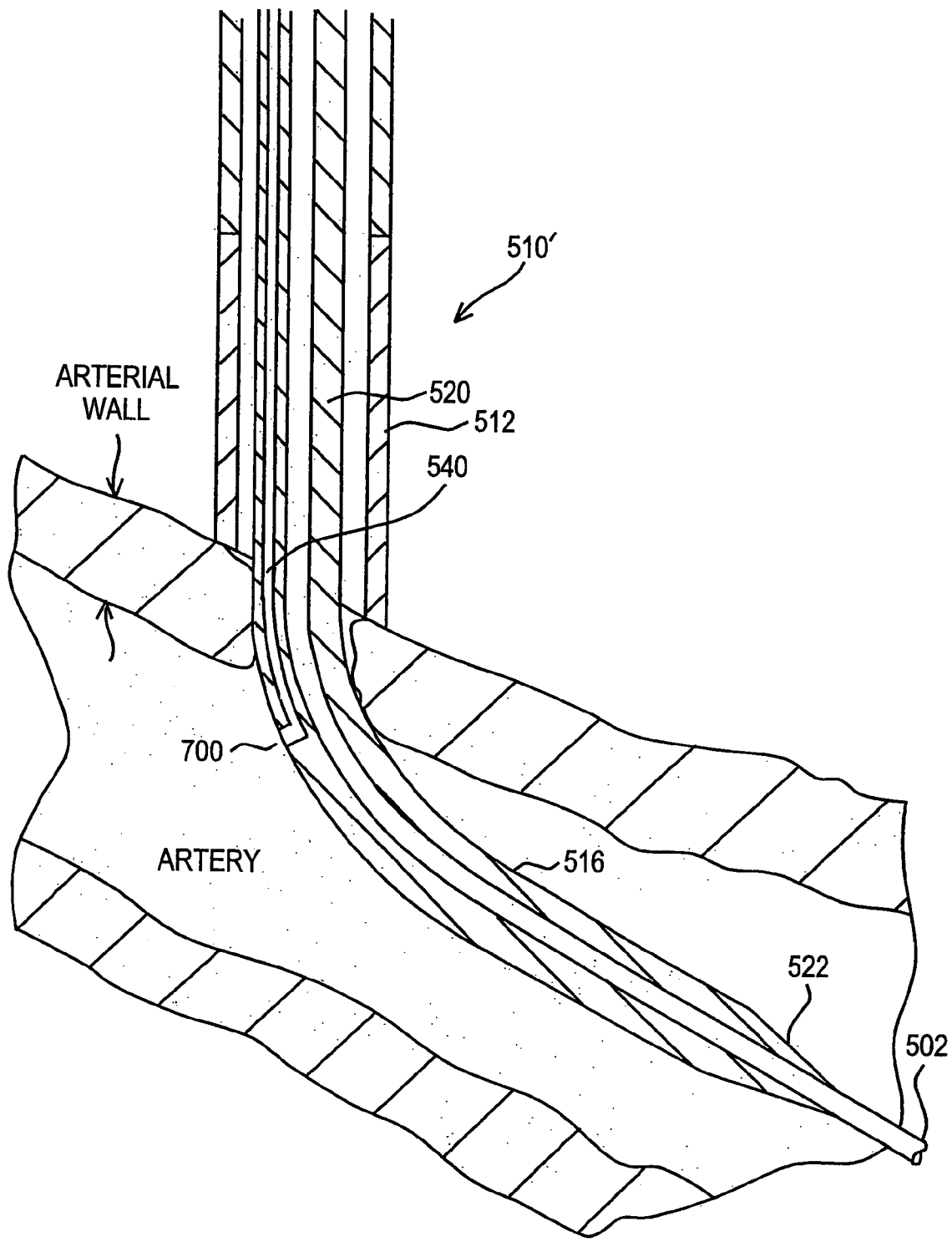
FIGS. 37 and 38 are isometric views of blood marking passageways of the introducer of the present invention.
Figure 38:
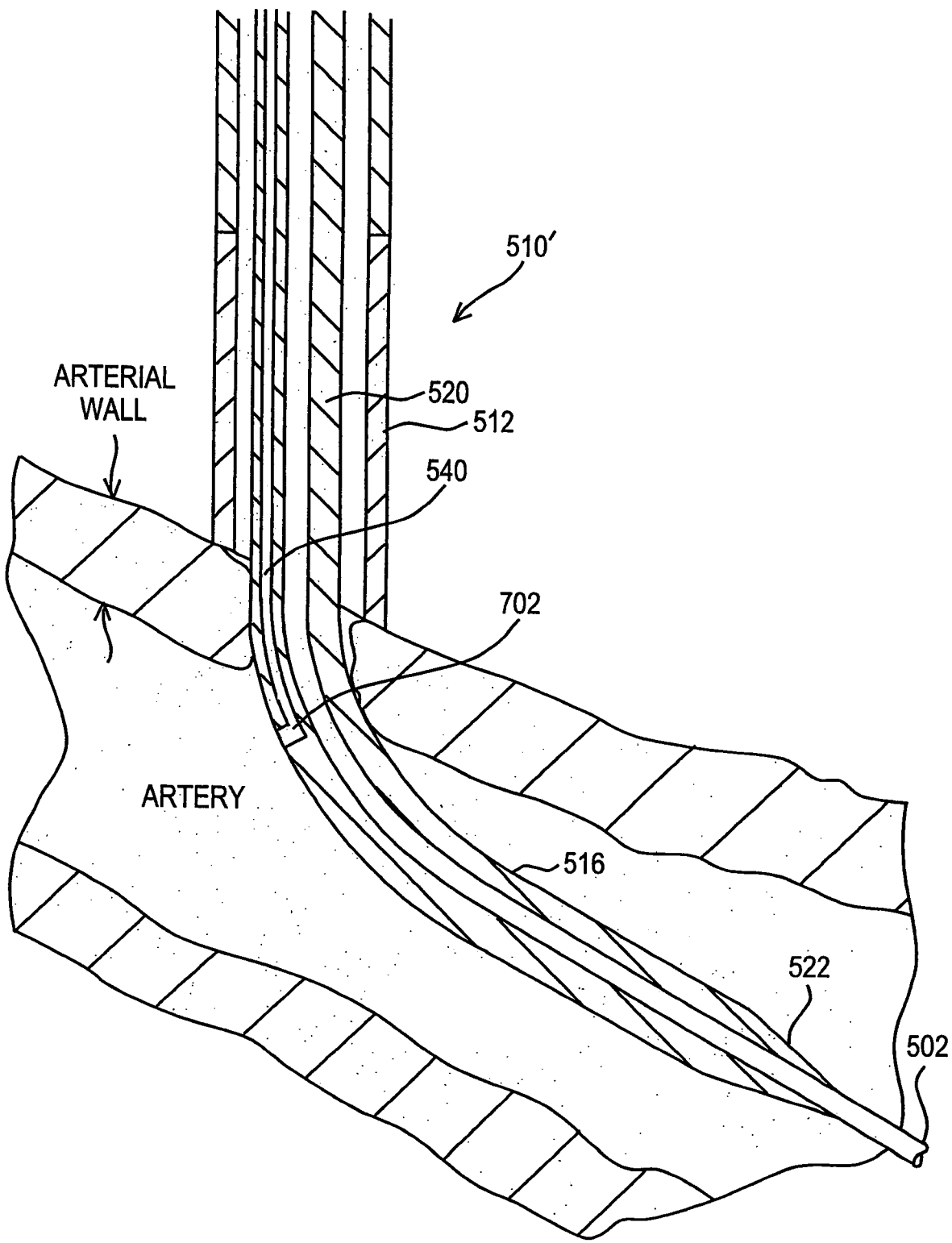

FIGS. 37 and 38 depict alternative embodiments for blood-marking. In FIG. 37, the BM lumen 540 includes a sensor 700 (e.g., differential pressure transducer, flow sensor, electrodes, etc.) to detect the presence of fluid or fluid flow thereon. The wiring for the sensor can be routed through the lumen 540, as shown, to transmit a signal of the pressure (or presence of fluid) at the sensor 700. In FIG. 38, an optical fiber 702 is placed in lumen 540 for direct viewing of the area around BM port.

Thus, the foregoing-described steps provide a method for identifying the depth of insertion of the transluminal device into an artery or vein based on the presence of pressurized blood internal to the vessel and the absence of pressurized blood external to the vessel. Alternatively, more than two blood marking points, lumens, and ports may be provided to further aid in determining precisely the depth of the inserted transluminal device. Furthermore, it is contemplated that the foregoing described insertion depth identifying technique may have utility in other contexts, as well, and those skilled in the art will recognize that the foregoing technique should not be limited to the context described hereinabove.

As described above, either the stabilization loop portion 680 or 680', or the guide sheath 662 may therefore be approximated to tissue surrounding the wound site, so as to cause spring tension against the surrounding tissue, thereby aiding in approximately centering an introducer about the wound site, as well as in allowing opposing sides of the tissue surrounding the wound site to approximate one another. It is further contemplated that alternatives of the embodiments described above may be implemented consistent with the invention for stretching the wound site and for centrally locating procedures at the wound site. For example, in the above-described embodiments, loop portions 680 and 680' provide a force to the wire and the guide sheath to spread the sheath outwardly and to approximate opposing portions of the wound site, as shown and described. However, in still other embodiments, the guide sheath can be formed having a biasing mechanism that forces the sheath into the opened or spread position as shown in FIGS. 31 and 36. To that end, this sheath may further comprise members on either side (such as the wire guides or shortened variations thereof shown in the embodiment of FIGS. 20A-22A) that provide the aforementioned outwardly opposing forces on the tissue surrounding the wound site.

There are many alternatives to the foregoing description of FIGS. 27-39 that will be apparent to those skilled in the art. For example, the wire forming, the loop structure described herein may be provided as a single continuous loop that is pre-threaded into the wire stabilization guides. In this case, the loop is closed by pulling on the free end of the loop. The wire may be snipped or cut so that it can be pulled free of the sheath and the wire stabilization guides. Other modifications may be made. For example, the sheath may be adapted with holding mechanisms (not shown) to hold the ends of the wire in place once the doctor has pulled on the free ends to form the loop. Still other modifications may be made. For example, instead of using wire in cooperation with the tubular wire stabilization guides to for the loop, the present invention contemplates that this arrangement can be replaced with as single elongated member (e.g. similar to the wire stabilization guide described herein) affixed to the guide sheath on opposing sides so that pulling this member forms the loop as shown in the drawings. In other words, the wire stabilization guide and wire described above may be replaced with a single member of sufficient modulus to for the loop as set forth herein.

The wire described herein may comprise a tube, filament, stranded filaments, or other structures that are equivalent.

Still other modifications can be made. For example the stabilization guides have been described herein as being generally tubular so that wire can be threaded therethrough. However, this is only an exemplary arrangement. The stabilization guides and wire could be coupled together in other configuration, for example, sliding engagement that may comprise a tongue-and-groove coupling, dovetail coupling, or other arrangement that would permit relative motion between the stabilization guides and the wire, while still providing mechanical strength along at least one axis. Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An introducer for guiding a wound closure means to a wound site and for configuring the wound site to receive the wound closure means comprising:
   a sheath having a lumen with a distal opening, the sheath being adapted to be located with its distal opening proximally adjacent of the wound site; and
   a pair of tissue-engaging stabilizers carried by the sheath and extending distally of the distal opening to enable the stabilizers to project through the wound site, the stabilizers being configured to engage opposed portions of the wound site and to apply outwardly opposing stretching forces to the wound site;
   whereby other opposing portions of the tissue surrounding said wound site between the stabilizers are caused to be drawn toward approximation in response to the outwardly opposing stretching forces.

2. The introducer of claim 1, wherein the stabilizers extend from laterally opposed locations on the sheath whereby engagement of the stabilizers with opposed portions of the wound site will position the sheath with its distal end approximately centered on said wound site.

3. The introducer of claim 1 further comprising:
   the stabilizers being defined by opposed portions of a stabilization loop; and
   an activation wire for deploying the loop in a configuration in which the opposed portions of the loop expand outwardly apart from each other.

4. The introducer according to claim 3 wherein said opposed portions of the stabilization loop are oriented at a diverging angle to span a distance greater than the diameter of the sheath when in a deployed configuration.

5. The introducer according to claim 3 wherein each of the stabilizers is attached at one end to the sheath and has a free distal end and when in said deployed configuration the distal ends of the stabilizers are adjacent each other to define a loop.

6. The introducer according to claim 5, wherein said actuation wire extends between said distal ends of the stabilizers.

7. The introducer according to claim 6 wherein said actuation wire is slidably disposed in at least one of the stabilizers.

8. The introducer according to claim 5 wherein the stabilizers are positioned on opposite sides of the sheath.

9. The introducer according to claim 5 wherein said two stabilizers extend an equal length from said sheath.

10. The introducer according to claim 5 wherein the stabilizers are of substantially unequal length.

11. The introducer according to claim 3 wherein said actuation wire comprises at least one reinforced section, said reinforced section having an orientation generally perpendicular to a central axis of said sheath when said stabilization loop is in said deployed configuration.

12. The introducer according to claim 3 wherein said sheath comprises at least one tear seam extending from said end of said sheath.

13. The introducer according to claim 12 wherein said sheath comprises at least one tear seam extending from said end of said sheath disposed on each side of said stabilization loop.

14. The introducer according to claim 3 further comprising a guide rod dimensioned to be slidably received within said sheath.

15. The introducer according to claim 14 wherein said guide rod comprises at least one recess sized to releasably retain at least a portion of said actuation wire.

16. A method for stabilizing a wound site comprising:
providing an introducer comprising a sheath having a lumen with a distal opening, and a pair of tissue-engaging stabilizers carried by the sheath and extending distally of the distal opening, the stabilizers being configured to engage opposed portions of the wound site and to apply outwardly opposing stretching forces to the wound site;
approximating to the wound site the sheath with the stabilizers projecting through the wound site; and
causing the stabilizers to apply outwardly opposing stretching forces to portions of the wound site so as to cause other opposing portions of the tissue surrounding said wound site to approximate one another.

17. The method of claim 16, wherein said sheath is held approximately centered on said wound site.

18. A method of stabilizing a wound comprising:
providing an introducer comprising a sheath having a lumen with a distal opening, the sheath being adapted to be located with its distal opening proximally adjacent the wound site and a stabilization loop carried by and extending from the distal end of said sheath;
inserting opposed portions of the stabilization loop into a wound; and
deploying said stabilization loop to expand the opposed portions outwardly to apply a stretching force to the tissue sufficient to cause tissue about the wound to be drawn together.

19. The method according to claim 18 wherein said stabilization loop comprises an actuation wire and causing outward expansion of the stabilization loop comprises retracting said actuation wire.

20. The method according to claim 19 wherein said stabilization loop comprises at least one tubular guide extending from said end of said sheath, and deploying said stabilization loop comprises approximating a distal end of the tubular guide to said end of said sheath.

21. The method according to claim 19 wherein said stabilization loop comprises a reinforced relatively inflexible intermediate segment, and wherein retraction of the actuation wire orients said reinforced section generally perpendicular to a central axis of said sheath.

22. The method according to claim 18 wherein the loop is expanded to a width greater than that of the sheath causing, in turn, expansion of the distal end of said sheath.

23. The method according to claim 22 wherein expanding the loop separates said end of said sheath at a slit.

24. The method according to claim 18 wherein said introducer comprises a guide rod slidable within said sheath, the method further comprising releasably attaching at least a portion of the stabilization loop to said guide rod and inserting at least a portion of said guide rod into said wound.

25. The method according to claim 24 further comprising disposing at least a portion of said stabilization loop in a recess in said guide rod.

26. The method according to claim 18 wherein deploying said stabilization loop orients the stabilization loop outwardly and at an angle relative to the sheath.

27. The method according to claim 26 wherein said outwardly angled stabilization loop applies outward forces on opposed sides of said wound.

28. The method according to 26 wherein said outwardly angled stabilization loop urges said sheath toward said wound.

* * * * *